(12) United States Patent
Ruchti et al.

(10) Patent No.: US 7,436,511 B2
(45) Date of Patent: Oct. 14, 2008

(54) ANALYTE FILTER METHOD AND APPARATUS

(75) Inventors: Timothy L. Ruchti, Gilbert, AZ (US); Alexander D. Lorenz, Chandler, AZ (US); Kevin H. Hazen, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 276 days.

(21) Appl. No.: 11/188,064

(22) Filed: Jul. 22, 2005

(65) Prior Publication Data
US 2006/0017923 A1 Jan. 26, 2006

Related U.S. Application Data

(60) Continuation-in-part of application No. 10/870,727, filed on Jun. 16, 2004, now Pat. No. 7,038,774, which is a division of application No. 09/664,973, filed on Sep. 18, 2000, now Pat. No. 6,864,978, which is a continuation-in-part of application No. 09/359,191, filed on Jul. 22, 1999, now Pat. No. 6,280,381.

(60) Provisional application No. 60/599,431, filed on Aug. 6, 2004, provisional application No. 60/116,883, filed on Jan. 22, 1999.

(51) Int. Cl.
G01J 3/28 (2006.01)
G01J 3/42 (2006.01)
G01J 3/427 (2006.01)
G01N 33/48 (2006.01)
A61B 5/00 (2006.01)

(52) U.S. Cl. .......... 356/326; 356/319; 356/39; 600/310; 600/316; 600/322; 600/365

(58) Field of Classification Search .......... None
See application file for complete search history.

(56) References Cited

U.S. PATENT DOCUMENTS

| | | | |
|---|---|---|---|
| 5,243,546 A | 9/1993 | Maggard | |
| 5,446,681 A | 8/1995 | Gethner et al. | |
| 5,459,677 A | 10/1995 | Kowalski et al. | |
| 5,710,713 A | 1/1998 | Wright et al. | |
| 5,857,462 A | 1/1999 | Thomas et al. | |
| 5,976,466 A | 11/1999 | Ratner et al. | |
| 6,061,582 A * | 5/2000 | Small et al. | 600/316 |
| 6,549,861 B1 | 4/2003 | Mark et al. | |
| 6,615,151 B1 | 9/2003 | Scecina et al. | |
| 7,038,774 B2 | 5/2006 | Hazen et al. | |

FOREIGN PATENT DOCUMENTS

WO WO 2004000113 A1 * 12/2003

* cited by examiner

*Primary Examiner*—L. G. Lauchman
*Assistant Examiner*—Gordon J Stock, Jr.
(74) *Attorney, Agent, or Firm*—Michael A. Glenn; Glenn Patent Group

(57) ABSTRACT

The invention comprises a method and apparatus for enhancing the analysis of noninvasive spectra, resulting in improved analytical performance. More particularly, the invention comprises a method and apparatus for processing noninvasive spectra with an analyte filter that preferably rejects variation likely to be detrimental to the measurement system, while passing signal that probabilistically is unique to the target analyte. Subsequently, the analyte filtered data are used to estimate an analyte property, such as a glucose concentration, in the presence of noise, interferences, state changes, and/or across analyzers.

78 Claims, 16 Drawing Sheets

ANALYTE FILTER METHOD AND APPARATUS

CROSS REFERENCE TO RELATED APPLICATIONS

This application claims benefit of U.S. provisional patent application Ser. No. 60/599,431 filed Aug. 6, 2004 and is a continuation-in-part of U.S. patent application Ser. No. 10/870,727 filed Jun. 16, 2004 now U.S. Pat. No. 7,038,774, which is a divisional of U.S. patent application Ser. No. 09/664,973 filed Sep. 18, 2000 now U.S. Pat. No. 6,864,978, which is a continuation-in-part of U.S. patent application Ser. No. 09/359,191, filed Jul. 22, 1999, now U.S. Pat. No. 6,280,381, which claims benefit of U.S. provisional patent application Ser. No. 60/116,883 filed Jan. 22, 1999.

BACKGROUND OF THE INVENTION

1. Technical Field

The invention relates generally to biomedical methods and apparatus. More particularly, the invention relates to processing spectra to yield enhanced analyte property estimations. Still more particularly, the invention relates to generating and using an analyte filter designed to an analyte signal shape in the presence of interference, preferably in combination with multivariate analysis.

2. Description of Related Art

Digital Filtering

The technique of digitally filtering collected data is performed to isolate a portion of the data. Digital filtering is broadly broken into two types, finite impulse response (FIR) and infinite impulse response (IIR). Digital filtering techniques are used to reduce or remove background effects, to reduce or remove high frequency noise, and to enhance signal. Specific sub-types of digital filtering have been previously described to process noninvasive near-infrared data to isolate chemical or physical information related to physiology, instrumentation, and/or the environment. Specific types of digital filtering, such as derivatives and Fourier filters are discussed here.

Derivative/Convolution

A. Savitsky and M. Golay, *Smoothing and differentiation of data by simplified least squares procedures*, Anal. Chem., 36, 1627-40, (1964) describe a convolution based implementation of smoothing, first derivative filtering, second derivative filtering, and higher order derivative filtering for enhancing the signal-to-noise ratio of a response or a vector.

D. Haaland, M. Robinson, G. Koepp, E. Thomas, and R. Eaton, *Reagentless near-infrared determination of glucose in whole blood using multivariate calibration*, Appl. Spect., 46, 1575-1578, (1992) describe the use of derivatives in conjunction with glucose concentration determination. The authors suggest use of derivative spectra for the reduction of subject-to-subject or inter-subject spectral variation.

J. Hall, Method and device for measuring concentration levels of blood constituents non-invasively, U.S. Pat. No. 5,361,758 (Nov. 8, 1994) describes the use of a derivative in processing of near-infrared noninvasive spectra. J. Samsoondar, Method for calibrating spectrophotometric apparatus with synthetic fluids to measure plasma and serum analytes, U.S. Pat. No. 6,470,279 (Oct. 22, 2002); J. Samsoondar, Method for calibrating spectrophotometric apparatus, U.S. Pat. No. 6,611,777 (Aug. 6, 2003); and J. Samsoondar, Method for calibrating spectrophotometric apparatus, U.S. Pat. No. 6,651,015; Nov. 18, 2003) describe the use of order derivatives to process spectra. The processed spectra are used on spectra collected on a second instrument to enhance calibration transfer developed on at least one additional instrument. In this document, an order derivative is also referred to as a mathematical derivative.

Fourier Filtering

M. Arnold, et. al., *Determination of physiological levels of glucose in an aqueous matrix with digitally filtered Fourier transformed near-infrared spectra*, Anal. Chem., 62, 1457-1464, (1990); G. Small, et. al. *Strategies for Coupling Digital Filtering with partial least-squares regression: application to the determination of glucose in plasma by Fourier transform near-infrared spectroscopy*, Anal. Chem, 65, 3279-3289, (1993); G. Small, M. Arnold Method and apparatus for non-invasive detection of physiological chemicals, particularly glucose, U.S. Pat. No. 5,459,317 (Oct. 17, 1995); and G. Small, M. Arnold, Method and apparatus for non-invasive detection of physiological chemicals, particularly glucose, U.S. Pat. No. 6,061,582 (May 9, 2000) describe the use of a Gaussian digital filter for processing absorbance data after transforming from a wavelength to a frequency domain.

Calibration Transfer

Overview

Calibration transfer is a standardization procedure designed to eliminate a full recalibration and to maintain information residing in the existing model. Calibration transfer is useful because sources of variation in the instrument and environment are modeled in the development of a training or calibration set. Therefore, as the instrument or environment state changes the model components does not exactly match the current state.

Identical performance of analytical instruments is unrealistic even with the successful implementation of tight quality control on instrument hardware. For example, variation in the output of a source, quality of lenses or mirrors, alignment, and detector response, which are limited by manufacturing tolerances, result in differences between spectrometers even of the same design. The instrument differences result in spectra of the master instrument varying from that of the slave instrument. Variations between the spectrometers result in errors when using a calibration developed on a spectrometer to determine parameters with a second spectrometer. Generally, this error is increasingly detrimental as the signal-to-noise ratio of the determined analyte decreases. Several techniques for calibration transfer are presented here.

Robustness

One approach to calibration transfer is to generate a robust model that covers all future conditions. Experimental design is used to develop a robust calibration. For noninvasive glucose concentration determinations, parameters include measurement conditions, such as temperature and humidity, as well as analyte/constituent concentration distributions. This approach is effective in controlled environments when the analyte signal-to-noise ratio is strong. However, the technique is not efficient in terms of time and money. Also, the quality of the calibration is suspect in terms of inability to predict future conditions that need to be incorporated into the original calibration. In addition, the technique does not readily allow incorporation of future conditions that are later identified without a new experimental design and development of a new or updated calibration.

Full Recalibration

Full recalibration of an analyzer is not preferable due to time requirements, technical expertise requirements, and expense. In addition, recalibration often fails to capture a full range of parameters, such as variations in the environment and instrument, thereby forcing additional recalibrations as the state of these parameters change.

Axis Standardization

Calibration transfer is used to compensate for changes to an axis, such as an x-axis or a y-axis. For spectrophotometric based determination, an approach to x-axis stability is to provide, with each sample or on a daily basis, a spectrum of a standard that is used to determine the x-axis. For adjustment of the x-axis in the near-infrared, polystyrene is often used. Additional near-infrared wavelength standards include rare earth oxides, such as holmium oxide, erbium oxide, and dysprosium oxide. Each standard or reference provides multiple peaks that are used to set or adjust the x-axis, such as a wavelength axis. In its broadest sense, any material that yields known or reproducible peaks for a given state is usable as an x-axis standard.

Calibration transfer is also used to adjust or compensate for changes to a y-axis. For example, a y-axis is commonly adjusted with a reference standard. Examples of diffuse reflectance standards in the near-infrared include polytetrafluoroethylene diffuse reflectance standards, such as diffuse reflectance standards that come with diffuse reflectances of 2, 5, 10, 20, 40, 60, 80, and 99%.

Another approach is the use of standards that simulate the target sample, such as a tissue phantom or intralipid. In its broadest sense, any material that yields known or reproducible transmittance, reflectance, or diffuse reflectance is usable as a y-axis standard.

A number of difficulties exist for remeasuring standards. First, instability of the sample creates difficulties in producing a spectrum that is constant across time. Second, reproducing the environment, which affects the resulting spectra is difficult. For example, temperature and humidity effect spectra. Third, movement of the analyzer is an issue due to alignment. For example, this is relevant when the analyzer is moved from a lab to a process line or from a laboratory or production facility to a hospital or home setting. Replacement of analyzer components also leads to generation of spectra that are not reproducible.

Diabetes

Diabetes is a chronic disease that results in improper production and use of insulin, a hormone that facilitates glucose uptake into cells. While a precise cause of diabetes is unknown, genetic factors, environmental factors, and obesity appear to play roles. Diabetics have increased risk in three broad categories: cardiovascular heart disease, retinopathy, and neuropathy. Complications of diabetes include: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance and hyperinsulinemia, which is also referred to as hypoglycemia. It continues to be beneficial to have increased accuracy and precision of estimation of glucose concentration from noninvasive spectra.

There remains an unsolved need for extracting data from spectral data, such as noninvasive spectra, that is useful in generating subsequent analyte property estimations. It would be advantageous to provide a method and apparatus for enhancing the analysis of noninvasive spectra, resulting in improved analytical performance within an instrument, across instruments, and across states using an analytical filter.

SUMMARY OF THE INVENTION

A method and apparatus for enhancing the analysis of noninvasive spectra resulting in improved analytical performance is presented. More particularly, the invention comprises a method and apparatus for preprocessing noninvasive spectra with an analyte filter that preferably rejects variations that are likely to be detrimental to the measurement system, while passing the signal that is most likely unique to the target analyte. Subsequently, the analyte filtered data are used to estimate an analyte property, such as a glucose concentration, in the presence of noise, interferences, state changes, and/or across analyzers.

DETAILED DESCRIPTION OF THE INVENTION

Figure 1:
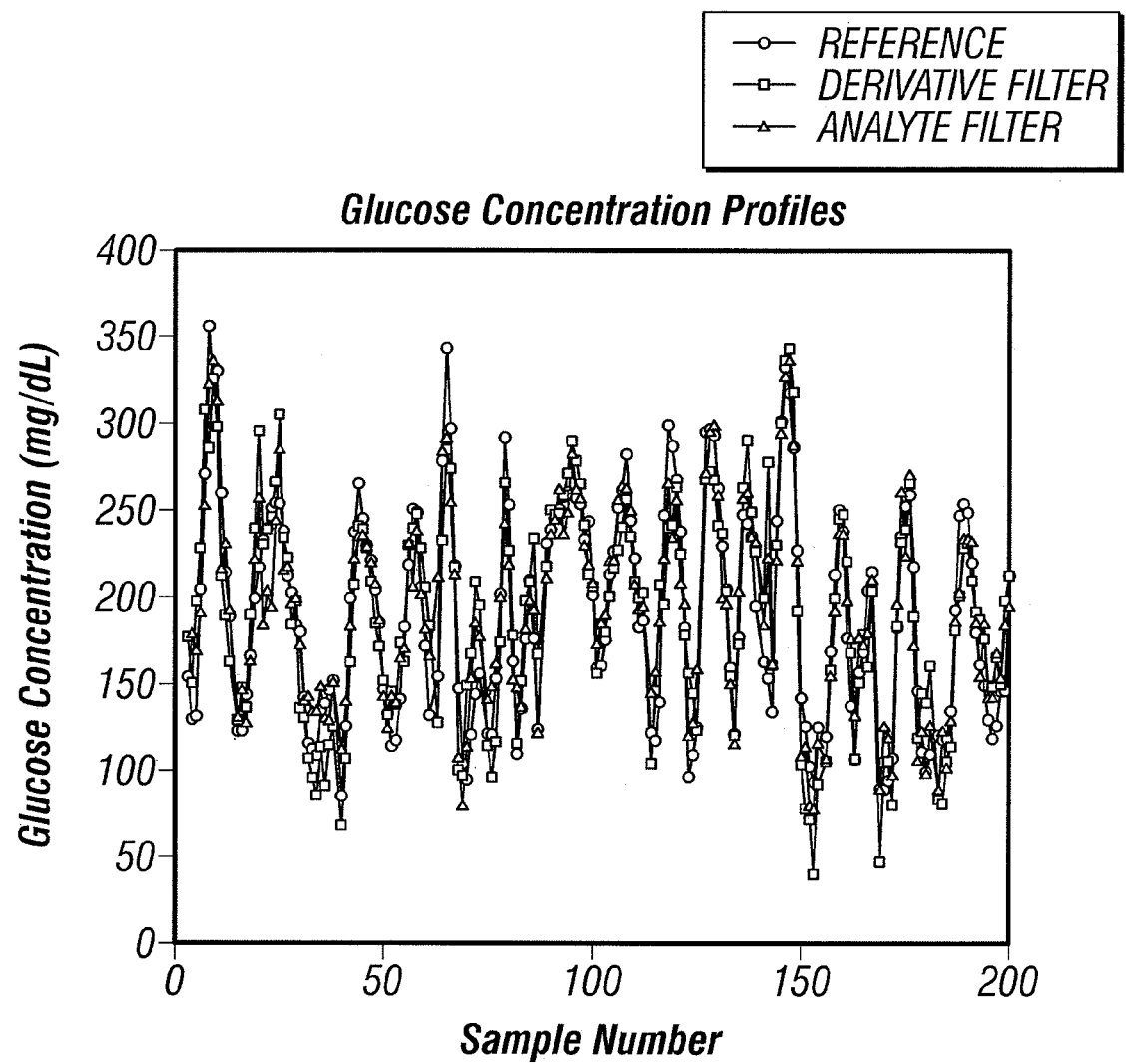
FIG. 1 provides reference and associated estimated glucose concentration profiles according to the invention.

The noninvasive measurement of blood and tissue analytes is accomplished through the application of a multivariate calibration model to a noninvasive spectral measurement. Although the developed model is designed to exploit the multivariate measurement and distinguish the analyte signal of interest from interfering signals, unaccounted for changes in the interference lead to degradation of the measurement performance. Types of unmodeled interference that can increase measurement error include instrument noise and performance changes, measurement artifacts, interfering analytes, changes in the optical properties of the tissue, and inconsistent optical coupling to the tissue.

To improve the robustness of a calibration with respect to sources of interference an analyte filter has been developed, which rejects variations that are likely to be detrimental to the measurement system, while passing the signal that is most likely unique to the target analyte. The filter is based upon shape information of the target analyte that is represented by the signal, net analyte signal, or extracted features preferably with compensation for interferences. To enhance the analyte filter functionality, the filter is optionally implemented in several stages, each stage being designed and optimized according to at least one criterion. The analyte filter is preferably further enhanced through a theoretical design that involves the use of interference models, in addition to shape information, to develop an optimized analyte filter. Finally, the filter is optionally used with a photo-detector array (PDA) to enhance noise rejection efficiency as compared to systems that use a single element detector and to improve measurement performance.

In a preferred embodiment of the invention, an analyte filter is used that preferably passes analyte related signal while suppressing interferences manifested as both high and low frequency noise. To illustrate the advantage of an analyte filter over a classical derivative type filter and to demonstrate how an analyte filter is used, an example is provided where noninvasive glucose concentration predictions are made using an algorithm. The example demonstrates that substitution of an analyte filter for a derivative processing step results in improved analytical performance. Further discussion follows Example I, which illustrates similar limitations in other filters. Still further discussion following Example I describes an analyte filter in more depth. The use of near-infrared noninvasive glucose concentration estimation in the example is illustrative in nature and is not intended to limit the scope of the invention.

EXAMPLE I

A data set is provided requiring multivariate analysis to derive an analyte property from a spectral data set. The data set, without modification, is processed separately first with a derivative filter and second with an analyte filter. Enhanced analyte property estimation is demonstrated with the analyte filter approach compared to the derivative filter approach demonstrating the advantage of an analyte filter over a derivative filter.

Instrumentation

A diffuse reflectance based glucose analyzer was used to collect calibration and estimation, also referred to as prediction, near-infrared spectra. The glucose analyzer included a sample module and a base module coupled by a communication bundle. The sample module included a source, backreflector, and optics. The communication bundle carried power and optical signal. The base module included a grating and a linear photo diode array detector. Wavelength and intensity references were collected and used. In this case, the wavelength reference was polystyrene and the intensity reference was polytetrafluoroethylene. The sample was a set of human forearms. Calibration data were collected with both a fixed probe and a floating probe, bottom-up measurement sampling the volar aspect of forearms, where the probe had a single bundlet. Prediction spectra were collected with a both a fixed probe and floating probe, in both bottom up and top down fiber probe configurations sampling both the volar and dorsal aspect of forearms with a single collection fiber. While the example is to a specific analyzer, the invention is applicable to data matrices generated from a wide number of related analyzers and sample sites, such as those described in U.S. patent application Ser. No. 10/472,856, which is incorporated herein in its entirety by this reference thereto.

Figure 12:
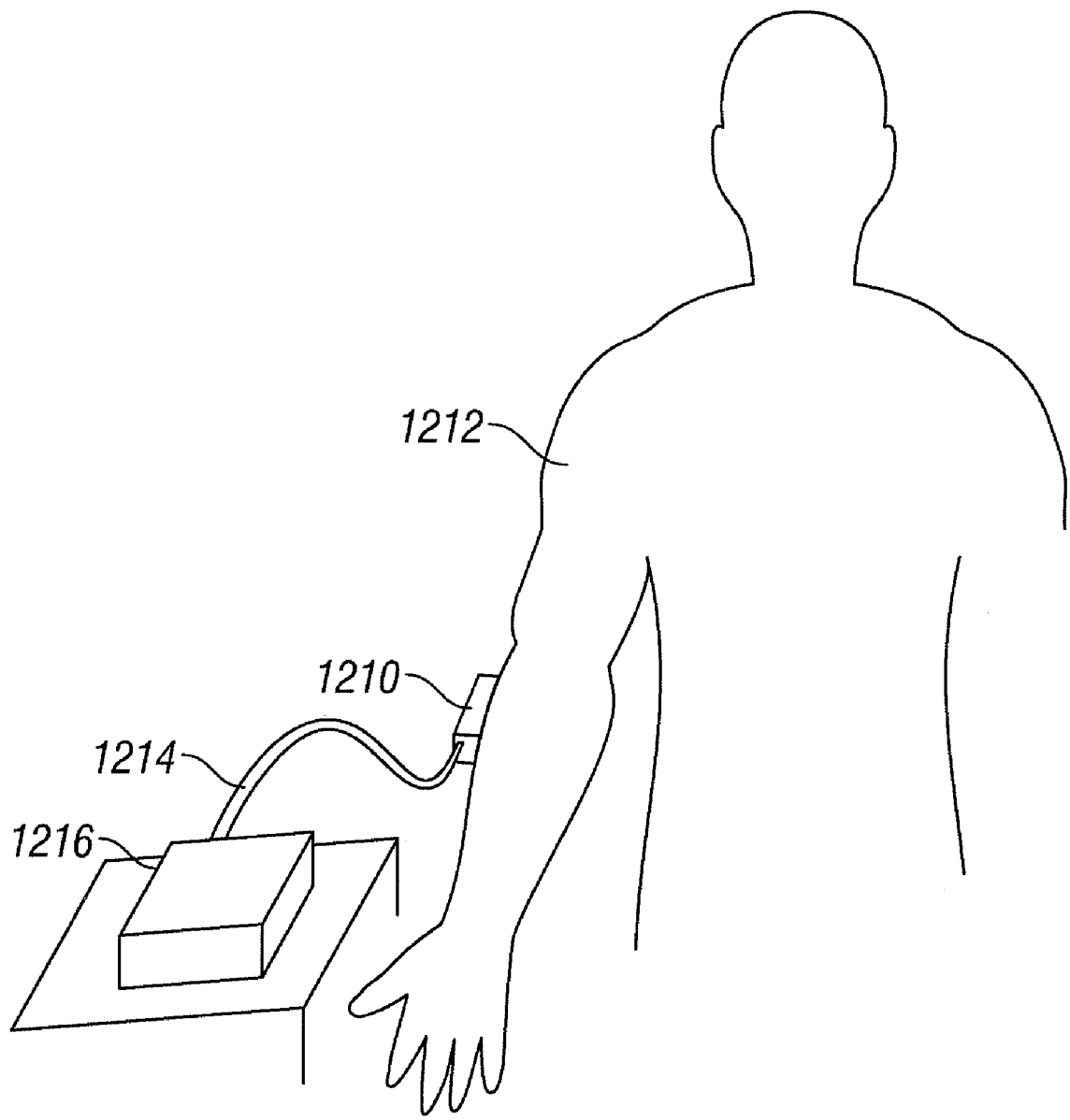
FIG. 12 shows a sampling module, a communication bundle and a base module.

The presently preferred embodiment of the invention uses a sampling module coupled to a base module. The sampling module includes an illumination system based upon an incandescent lamp. The base module includes a grating and detector array. The base module may be connected to the sampling module through a communication bundle. In this document, the combined sampling module, communication bundle, base module, and associated electronics and software is referred to as a spectrometer and/or glucose analyzer. In FIG. 12, the sampling module 1210 is semi-permanently attached to the forearm of a subject 1212, a communication bundle 1214 carries optical and/or electrical signal to and/or from a base module 1216 located on a table, and the communication bundle carries power to the sampling module from the base module.

Figure 13:
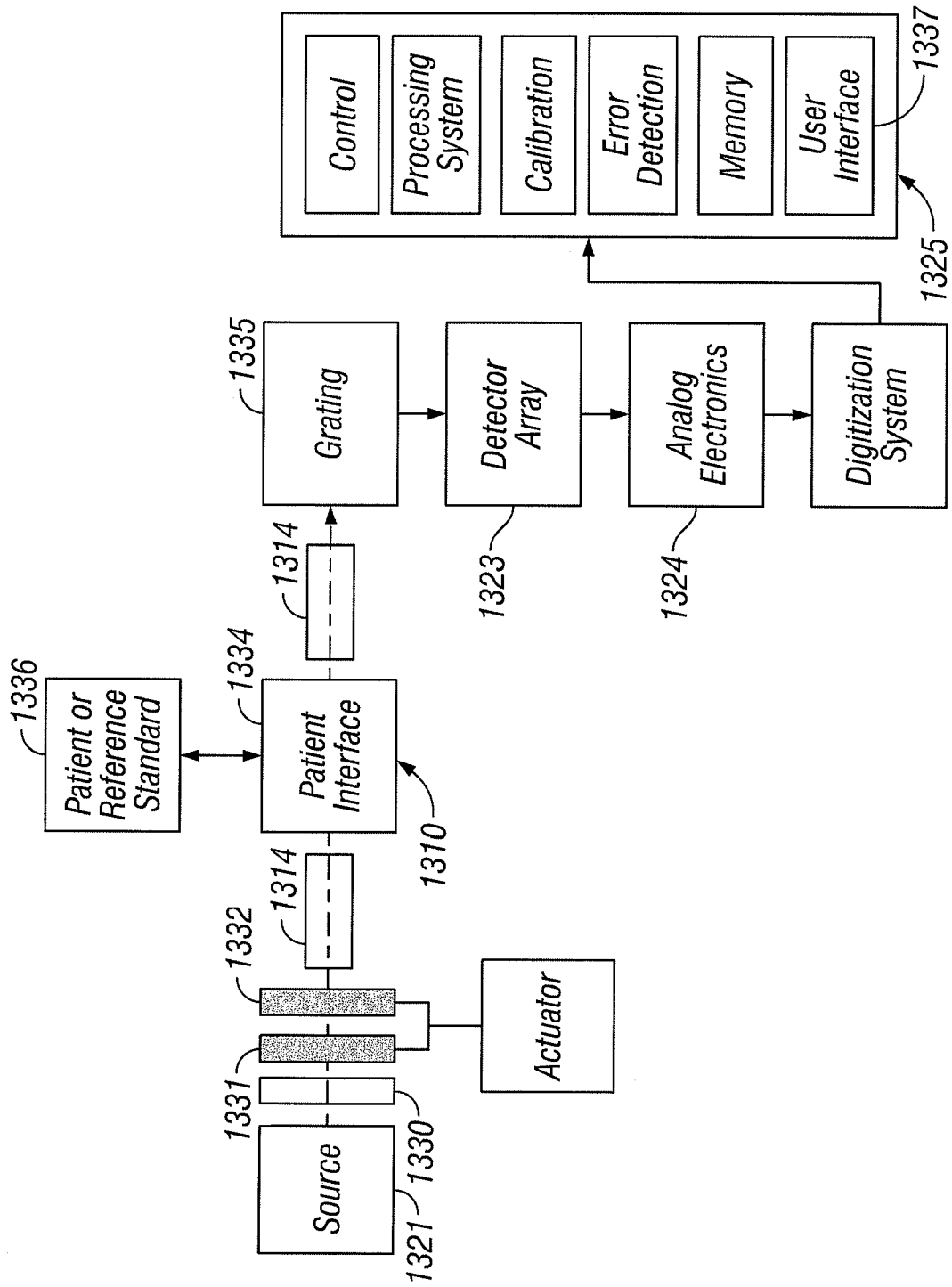
FIG. 13 shows a preferred embodiment with a grating and detector array.

A block diagram of the noninvasive glucose analyzer is provided in FIG. 13. Essential elements of the glucose analyzer are the source 1321, guiding optics 1314 before and/or after the sample for coupling the source to the sample and the sample to the detector(s) 1323, detector(s) and associated electronics 1324, and data processing system 1325. In FIG. 13, an optional optical filter 1330, light blocker 1331, and standardization material 1332 are shown. These components may also be positioned after the sample and before the detector. Variations of this simple block diagram are readily appreciated and understood by those skilled in the art.

The sampling module, base module, and communication bundle are further described herein. Key features of the invention may include but are not limited to: a semi-permanent patient/instrument interface sampling module 1310 incorporating at least one of a low profile sampling interface 1334, a low wattage stabilized source 1321 in close proximity to the sampled site, an excitation collection cavity or optics, a guide, a preheated interfacing solution such as fluorinert, a temperature controlled skin sample, a mechanism for constant pressure and/or displacement of the sampled skin tissue, a photonic stimulation source, and collection optics or fiber.

In the preferred embodiment the sampling module protrudes less than two centimeters from the skin measurement site. The sampling module may interface with a guide that may be semi-permanently attached to a sampling location on a human body. The guide aids in continuously and/or periodically physically and optically coupling the sampling module to the tissue measurement site in a repeatable manner with minimal disturbance. In addition, the guide in combination with the sampling module is responsible for pretreatment of the sample site for providing appropriate contact of the sampling device to the skin for the purpose of reducing specular reflectance, approaching and maintaining appropriate skin temperature variation, and inducing skin hydration changes. The sampling module preferably collects a diffusely reflected or transflected signal from the sampled region of skin.

In the preferred embodiment, the base module or semi-remote system includes at least a wavelength selection device such as a grating 1335 and a detector preferably a detector array with an optional wavelength reference standard 1336 such as polystyrene and an optional intensity reference standard such as a 99% reflective LABSPHERE. disk. The remote system is coupled to the sampling module via a communication bundle 1314 that carries as least the optical signal and optionally power. Additionally, the communication bundle may transmit control and monitoring signal between the sampling module and the remote system. The remote system has at least one of an embedded computer, a display 1337, and an interface to an external computer system. The remote system may be in close proximity to the guide element.

In one version of the invention, the sampling module and base module are integrated together into a compact handheld unit. The communication bundle is integrated between the two systems.

Figure 14:
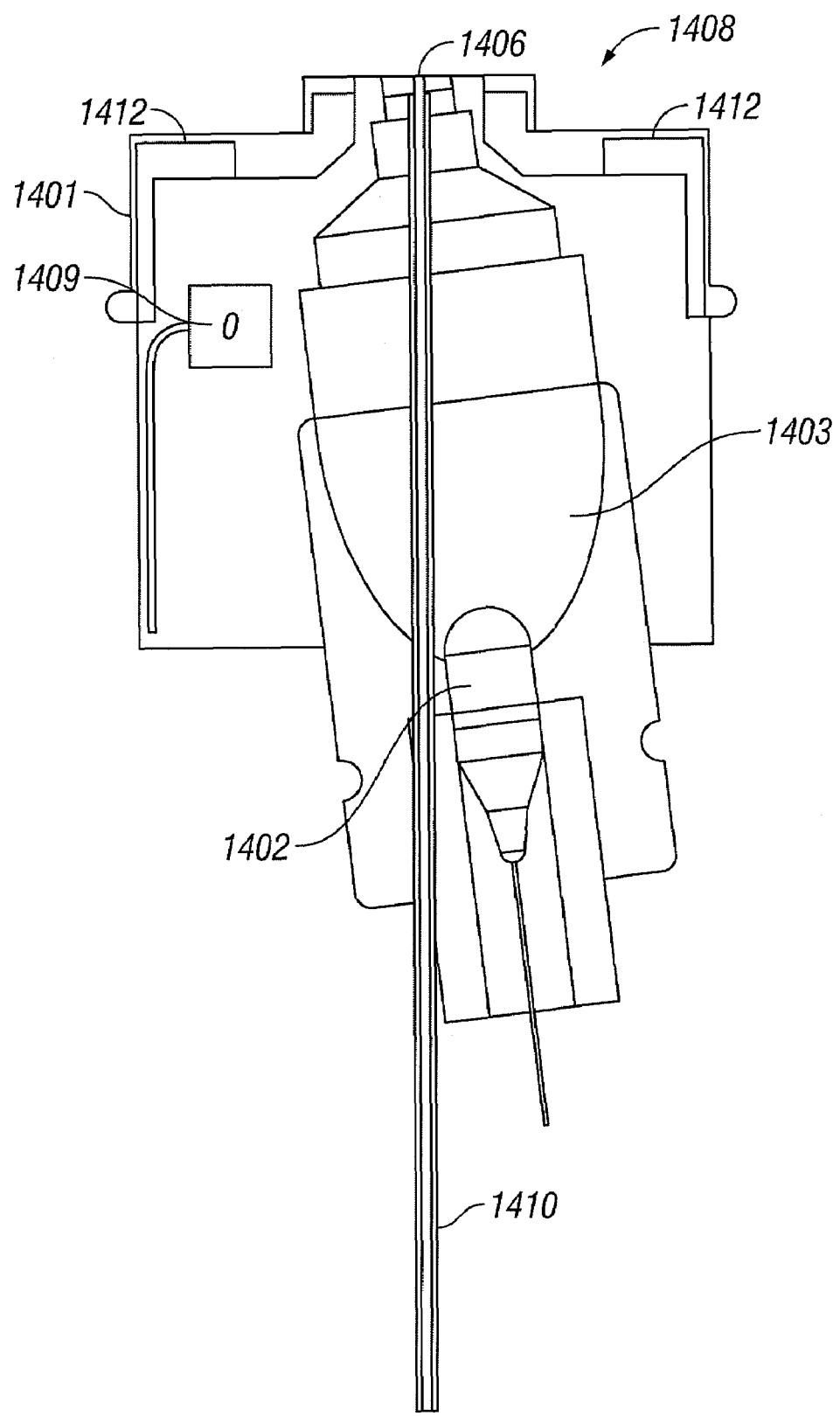
FIG. 14 shows a preferred embodiment of the sampling module.

One version of the sampling module of the invention is presented in FIG. 14. The housing 1401 is made of silicon. The lamp 1402 is a 0.8 W tungsten halogen source (Welch-Allyn 01270) coupled to a reflector 1403. A photodiode 1409 is used to monitor the lamp and to keep its output stable through the use of a lamp output control circuit, especially right after power-up. The reflector, and hence the incident light, is centered on an angle six degrees off of the skin's normal to allow room for a collection fiber. The light is focused through a 1 mm thick silicon window 1406 onto an aperture at the skin. The silicon operates as a longpass filter. The illuminated aperture of the skin has a 2.4 mm diameter. Positioning onto a sampling site is performed through a guide. The patient sampling module reversibly couples into the guide for reproducible contact pressure and sampling location. Magnets 1412 are used in the guide to aid in the positioning of the probe, to ensure proper penetration of the probe into the guide aperture and to enable a constant pressure and/or displacement interface of the sampled skin 1408. The reversible nature of coupling the sampling module into the guide allows the sampling module to be removed and coupled to an intensity reference and/or a wavelength reference that have the same guide interface and are preferably housed with the base module. The preferred intensity reference is a 99% reflective LABSPHERE material and the preferred wavelength reference is polystyrene. The preferred sampling module uses a heater for maintaining the skin at a constant temperature. A 600 μm detection fiber 1410 collects diffusely reflected light from the center of the silicon window. The detection fiber is coated in a manner to block source photons from penetrating through the cladding to the core. For example a metal sheath may be placed around the detection fiber. In this configuration, the length of the detection fiber is 0.7 meters. The communication bundle includes a power supply from the base unit. A blocking mechanism may be included to allow the detection of detector dark current or baseline. The base module incorporating a grating, detected array, associated electronics, and associated software is coupled to the sampling module via this bundle. In this configuration, the sampling module extends roughly three inches from the arm.

Spectrometer

It is here noted, that variation of one component may affect optimal or preferred characteristics of other components. For example, variation in the source may affect the quality or design of the. reflector, the thickness of the filter, the used aperture size, the time or power requirements for maintaining or heating the skin and/or fluorinert, and the diameter of the collection fiber. Similarly, changing another component such as the collection fiber diameter impacts the other elements. Those skilled in the art will appreciate the interaction of these elements. Those skilled in the art will also immediately appreciate that one or more components of the spectrometer may be changed without altering the scope of the invention.

Important regions to detect are permutations and combinations of bands due to water centered about 1450, 1900, or 2600 nm, protein bands centered about 1180, 1280, 1690, 1730, 2170, or 2285 nm, fat bands centered about 1210, 1675,1715,1760, 2130, 2250, or 2320 nm, or glucose bands centered about 1590, 1730, 2150, and 2272 nm.

A preferred physical orientation of the spectrometer is in a vertical position. For example, when sampling on the dorsal aspect of the forearm when the palm is face down on a support it is preferable for the sampling module to come down onto the arm from above. This allows the weight of the sampling module to be reproducible.

Figure 15:
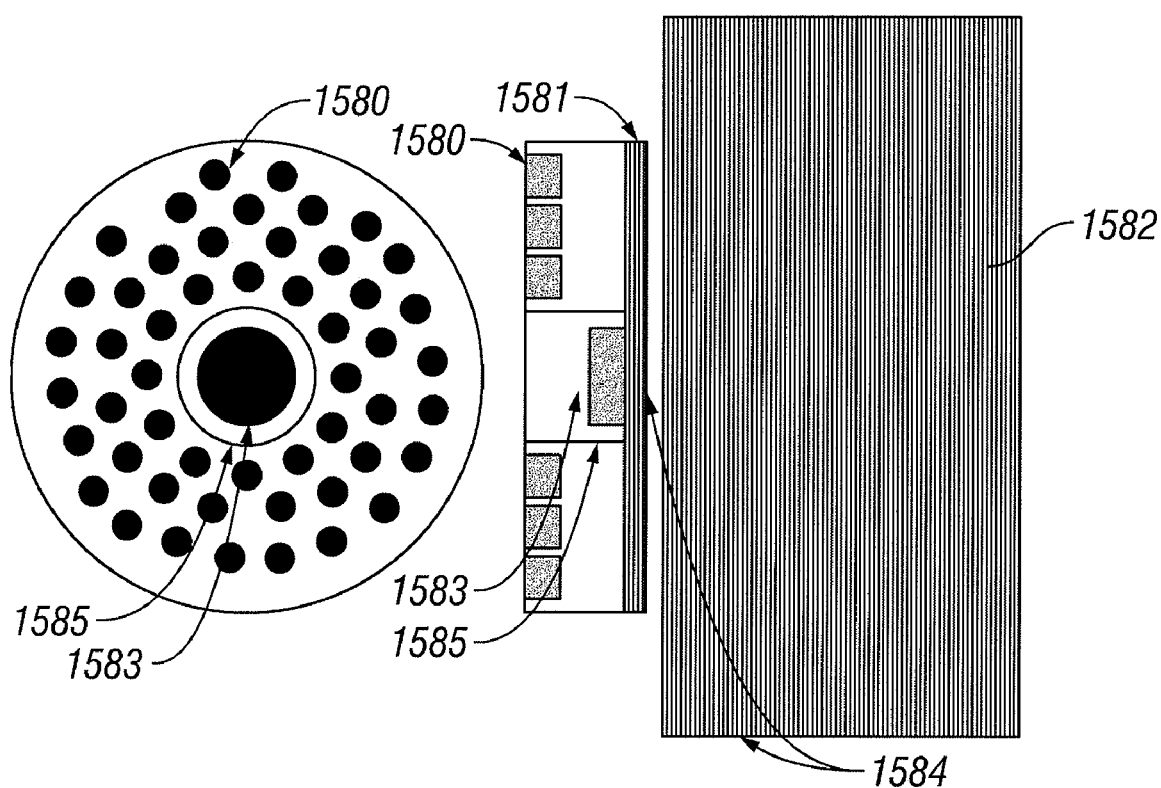
FIG. 15 shows an LED based embodiment of the sampling module.

In FIG. 15, a coupling fluid 1584, as disclosed above, is shown between the device and the tissue sample. An optional mixing chamber with a reflective surface may be used between the LEDs 1580 and the optical window 1581 to provide a nearly uniform distribution onto the tissue region 1582 surrounding the detection fiber 1583. A spacer 1585 may also be provided between the fiber and the LEDs. In this embodiment, the LEDs are designed with a bandwidth enabling the measurement, and the LEDs are arranged in a manner that allows the sampling and detection of a particular tissue volume at a particular band of wavelengths.

Figure 16:
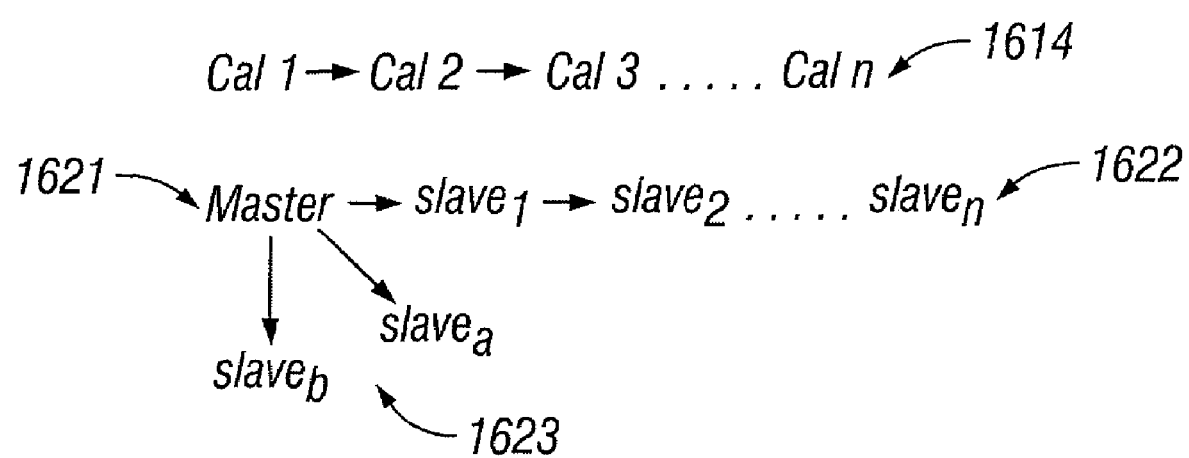
FIG. 16 provides a flow diagram of a method of generating calibration models by transferring a master calibration to slave calibration models.

Referring now to FIG.16, a process of calibration transfer is shown. Calibrations 1614 are required for each of n clusters. A master calibration 1621 is calculated for a first cluster. Then, the master calibration is transferred to slave calibrations to provide calibrations for each of the remaining n clusters. In this case, calibration transfer refers to the process of transforming spectra on a slave instrument to match the characteristics of the master such that the master calibration can be applied to the slave spectra. For clusters, calibration transfer refers to the process of transforming spectra on a slave instrument to match the characteristics of the master, such that a new calibration is generated that satisfies the specification of a cluster other than the one for which the master cluster was developed.

The clusters may also be organized into groups of clusters, so that the master calibration is transferred to slave calibrations 1623, which in turn are transferred to the slave calibration for the various clusters within each group.

Prior art methods of calibration transfer have been unsuccessful at modeling the complexity involved in providing calibration models for large numbers of instruments. Classifying the spectral measurements into clusters having a high degree of internal consistency reduces the complexity of the problem to a level that makes it possible to apply calibration transfer to large numbers of instruments. Clustering the acquired spectra into a limited number of subgroups allows the calibration transfer issues to be broken up into subsets, so that only a subset of the overall issues needs to be addressed between any two clusters. The result is that within a given cluster, all of the spectra have the same characteristics. A calibration is generated for a given cluster using spectra of samples containing the limited number of characteristics of that cluster. This eliminates having to deal with all of the variations possible in the raw measurements, significantly reducing the complexity that needs to be modeled by the calibration. Thus, the calibration used for a given cluster has instrument variations included in the model that are similar to variations resulting from the analyzer employed. Because each cluster has its own specification, the calibration transfer technique need only concern the differences between those two clusters. For example, if the only difference between the clusters is a linear x-axis shift, then the calibration transfer technique need only concern that parameter. This allows a more specific calibration transfer technique to be employed that is more robust, resulting in fewer factors because fewer instrument variations need to be modeled. This results in analysis of lower concentration analytes due to retention of signal to noise in the calibration transfer step.

Data Set

The analyzers used in this example were used to collect a calibration, monitoring, and independent estimation or prediction data set of noninvasive spectra with correlated glucose concentrations. The calibration, monitoring, and independent estimation data sets are used with the derivative processing and analyte filtering approach below. The calibration matrix represents 1109 spectra collected on a total of six subjects using two analyzers over an eight week period. The monitoring data set includes 1549 spectra collected on six subjects using a total of two analyzers over a period of twenty weeks. The estimation or prediction data matrix represents 188 samples from nine different subjects collected over a total of twelve visits using a total of seven analyzers over a period of multiple weeks. Prediction data sets are preferably generated with analyzers not used to generate the calibration data set or multivariate model.

Data Analysis

Multivariate models are typically generated or used with filtered or preprocessed spectra. Multivariate models extract information correlated with the reference values, such as glucose concentrations associated with each spectra. Multivariate models also correlate spectral features, such as baseline variation, noise, and interferences to the reference. Therefore, filters that pass features, such as a baseline deviation, correlated interference absorbance bands, and high-frequency noise, degrade the subsequent model performance in terms of precision, accuracy, and/or robustness. Therefore, an analyte filter designed to the frequency response of the analyte shape of the analyte and further designed to minimize interference benefits data analysis when multivariate models are employed.

Referring now to FIG. 1, the independent prediction data set collected with the instrumentation described, supra, is represented. The reference glucose concentrations are presented as a function of sample number, which is a nonlinear time axis. The glucose concentration profiles cover a wide dynamic range and break correlations with parameters, such as time and temperature. The independent reference concentrations are overlaid with glucose concentration estimations using: (1) an algorithm using an order derivative filter; and (2) an algorithm using an analyte filter. Both the derivative filter and analyte filter are described, infra.

The data set collected with the instrumentation described, supra, is processed with separate algorithms: one having an order derivative filter and another having an analyte filter. Both the order derivative filter and the analyte filter were generated using an optimization routine that used a calibration data set and a monitoring data set. The optimal order derivative filter and analyte filter were then each applied to an independent prediction data set. Results for both approaches are summarized herein.

The first order derivative approach preprocesses the spectra in three steps: 1) a 27-point first order derivative Savitsky-Golay convolution; 2) selection of a data matrix associated with the 1150 to 1850 nm spectral range; and 3) mean centering. Iterative preprocessing of the calibration and monitoring data sets while varying all of the derivative filter parameters results in the above described filter in combination with a principal component regression (PCR) using an optimized total of 44 factors. The resulting standard error of estimation, which is also loosely referred to as a standard error of prediction (SEP), on the new samples is 30.0 mg/dL. Within this data analysis, a 27-point first order derivative filter is determined to be optimal.

Figure 2:
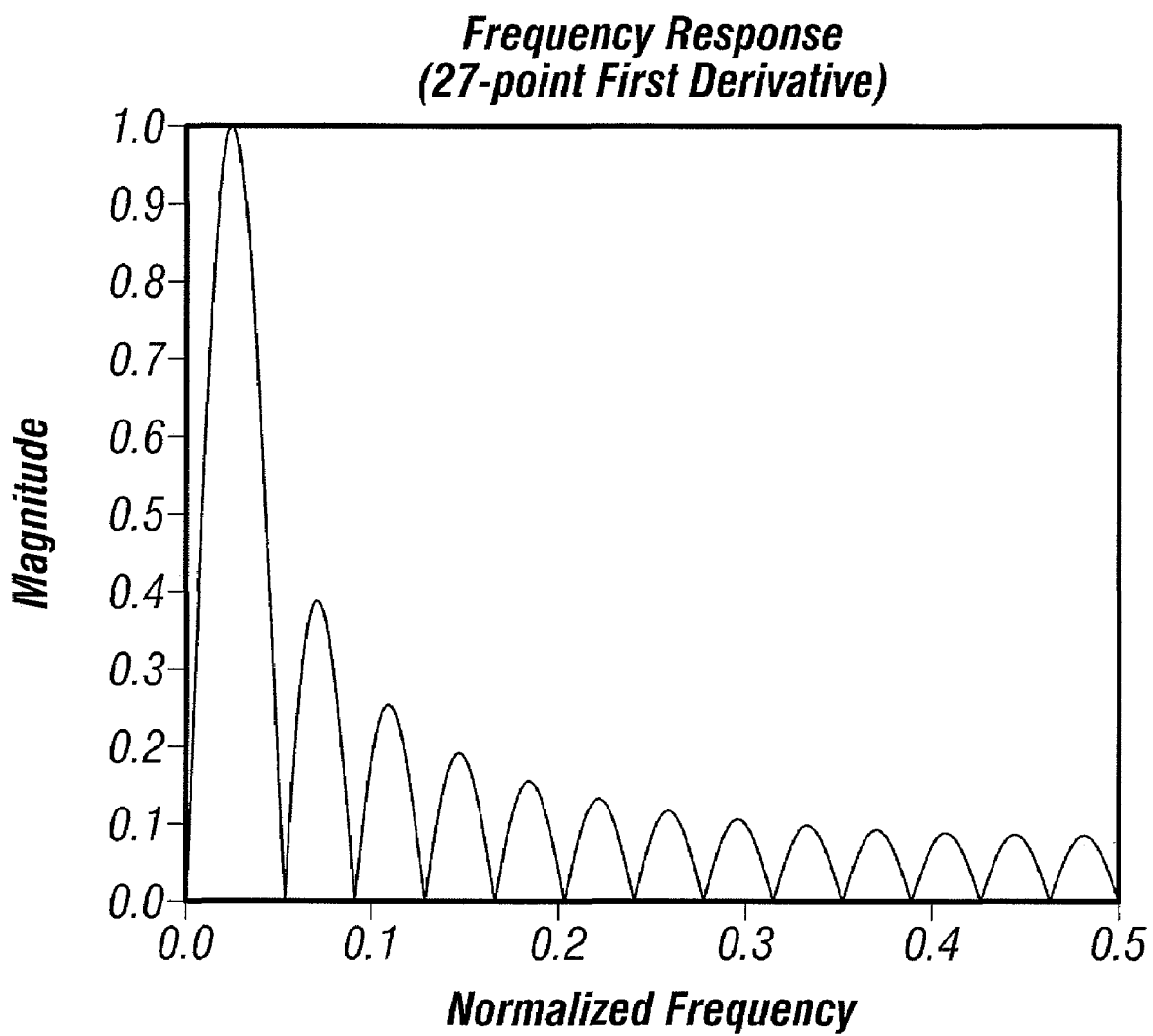
FIG. 2 illustrates a 27-point Savitsky-Golay first derivative filter.
Figure 4:
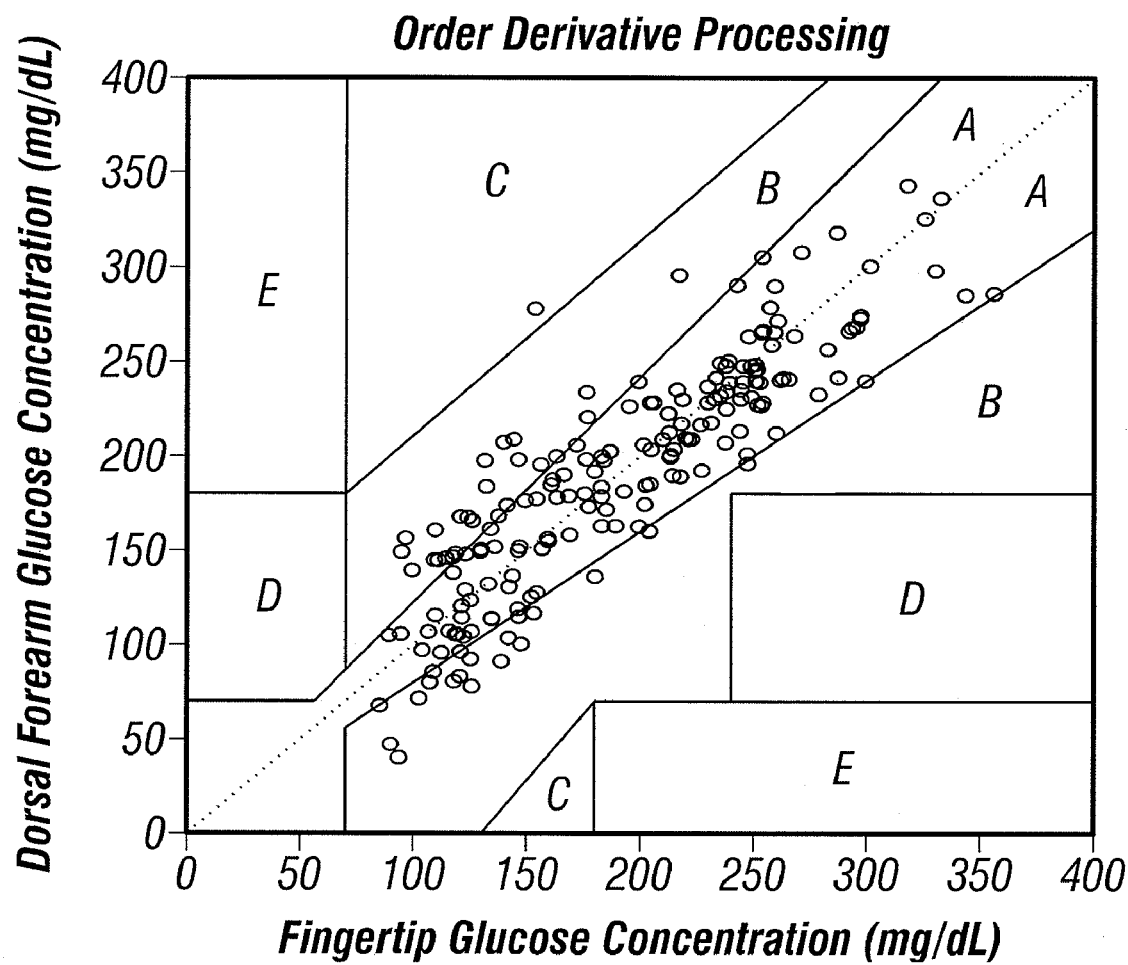
FIG. 4 provides derivative processed glucose concentration estimations overlaid onto a Clarke error grid.

Referring now to FIG. 2, the frequency response of the 27-point first order derivative filter is represented. The filter has a peak response at approximately 0.025 normalized frequency units and has multiple sub-peaks that pass higher frequency signal and noise. As shown below, this filter is substantially different than the analyte filter as the order derivative filter leaks high frequency noise. Using this optimal first order derivative filter and associated processing, the independent prediction data set is analyzed. The resulting glucose concentration estimations are presented in FIG. 4, which is overlaid onto a Clarke error grid. A total of 74.5, 25.0, and 0.5% of the resulting glucose estimations fell into the A, B, and C regions of a Clarke error grid, respectively. The resulting F-value is 3.75.

Figure 3:
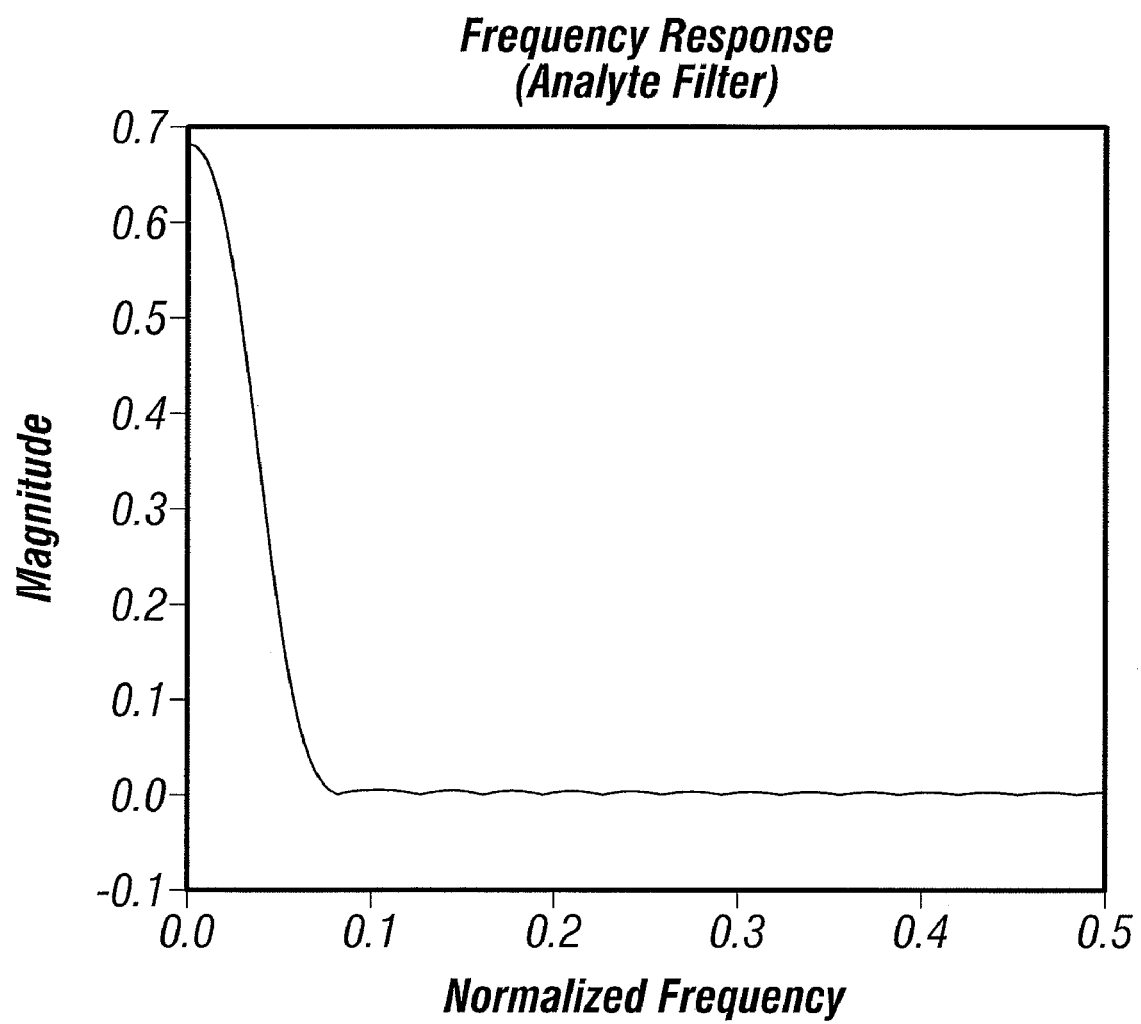
FIG. 3 provides an analyte filter according to the invention.

The analyte filter approach preprocesses the spectra in three steps: 1) processing with the analyte filter shown in FIG. 3; 2) selection of a data matrix associated with the 1150 to 1850 nm spectral range; and 3) mean centering. Referring now to FIG. 3, the analyte filter is represented in a frequency response format. The analyte filter reduces baseline deviation and extensively attenuates high frequency noise. The result is a filter that is substantially different than a zero, first, second, or higher order derivative filter. This particular filter uses a 0.04 normalized frequency units low-pass filter in combination with a 0.02 normalized frequency units high-pass filter. In this example, both the low-pass and high-pass filters are thirtieth order filters, though a large range of orders and cut-on or cut-off parameters are alternatively used. The analyte filter is non-symmetrical and is represented as the product of the low-pass filter and the high-pass filter. As above, optimizing the filter parameters while optimizing the multivariate model using a calibration and monitoring data set results in a principal component regression model using an optimized total of 36 factors.

Figure 5:
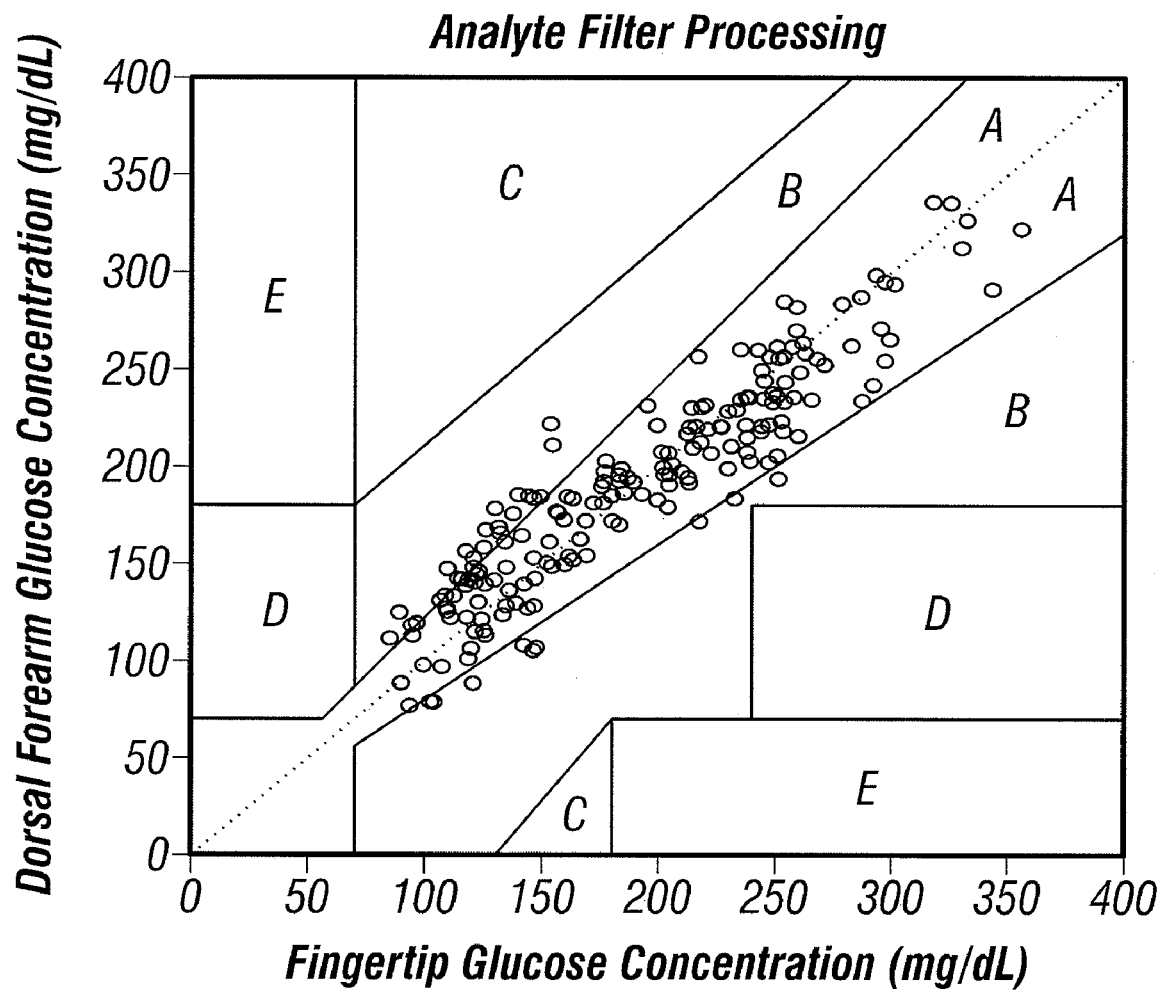
FIG. 5 provides combined filter processed glucose concentration estimations according to the invention overlaid onto a Clarke error grid.

Using this analyte filter and the associated processing, the independent prediction data set is analyzed. The resulting standard error of estimation, which is also loosely referred to as a standard error of prediction (SEP), on the new samples is 23.4 mg/dL. The resulting glucose concentration estimations are presented in FIG. 5, which is overlaid onto a Clarke error grid. A total of 81.9, 18.1, and 0.0% of the resulting glucose estimations fell into the A, B, and C regions of a Clarke error grid, respectively. The resulting F-value is 6.16. Comparing the results from the analyte filter approach and the first-order derivative approach results in glucose estimations with 22% less error, a higher F-value, a greater percentage of data points resulting in the desirable A region of the Clarke error grid and no data points falling into the undesirable C region of the Clarke error grid. Clearly, the analyte filter outperforms the optimized derivative filter. The improved success of the analyte filter approach is at least in part due to the removal of high frequency noise passed by the first-order derivative approach.

Of particular importance is the fact that a variety of analyte filters are produced that have the common characteristics of greatly attenuating high normalized frequencies, reducing low normalized frequencies, having a peak response near the analyte frequency response, and not being forced into a symmetrical or constrained shape.

Figure 6:
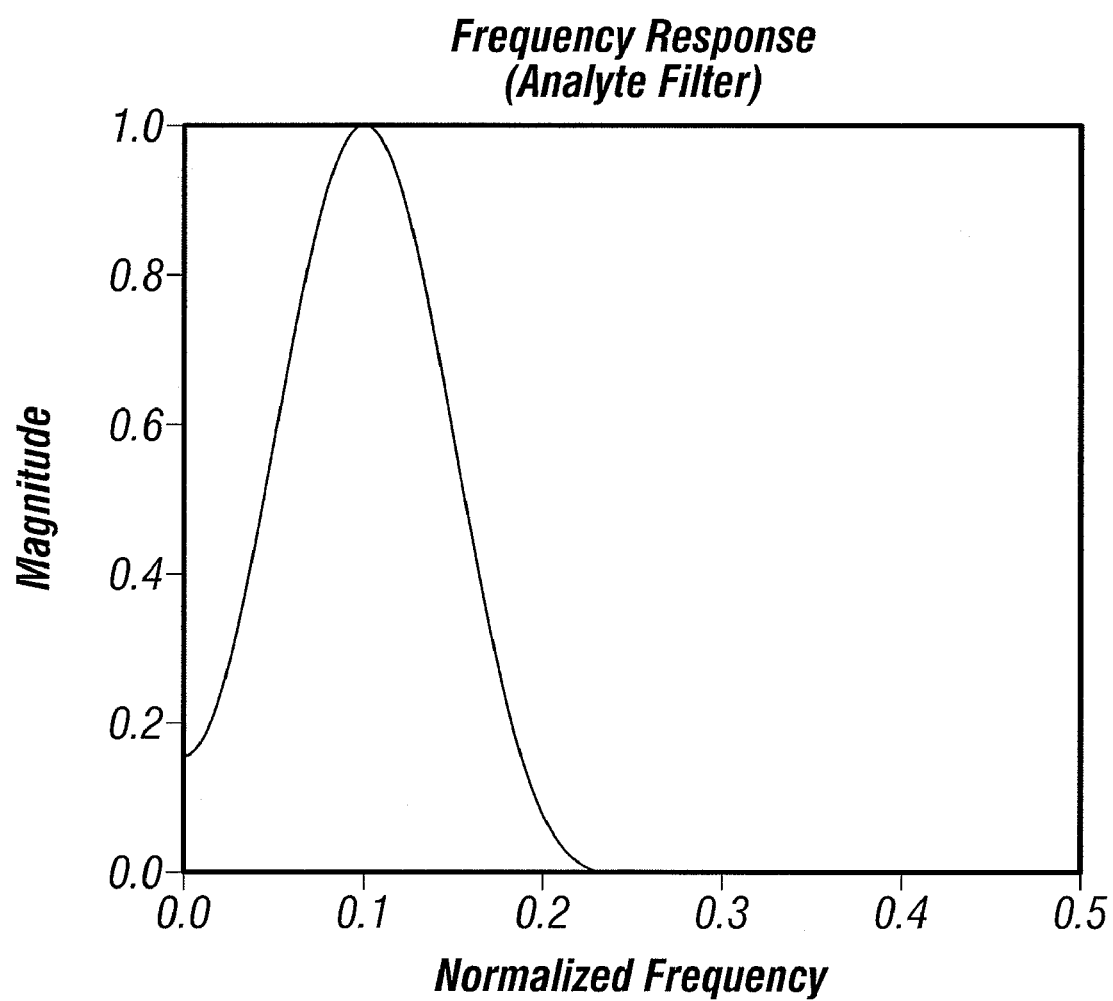
FIG. 6 provides an analyte filter according to the invention.

Referring now to FIG. 6, a second example of an analyte filter is provided where low frequency noise is reduced, high frequency noise is greatly attenuated, and the filter is non-symmetrical. The following section details how many non-analyte filters fail in one or more of these parameters.

Filters

A subset of digital filtering spectra is processing spectra with an order-derivative, such as a zero, first, second, or higher order derivative. As demonstrated herein, derivative filters pass high frequency spectral information. Another subset of digital filtering spectra is processing spectra with a symmetrical filter, such as a Fourier filter. Both of these filter types use responses that are restricted or constrained. That is, setting a particular filter efficiency at two or more frequencies forces particular filter responses at other frequencies that is detrimental. This detrimental response is described in detail in the subsequent paragraphs. Analyte filters, as defined herein, do not carry the restraint of low degrees of freedom, of forcing a magnitude of a frequency response at an $n^{th}$ frequency based upon the magnitude of the frequency response at a first, second, third, or fourth frequency, or being forced to be symmetrical.

Order Derivative Filters

Figure 7:
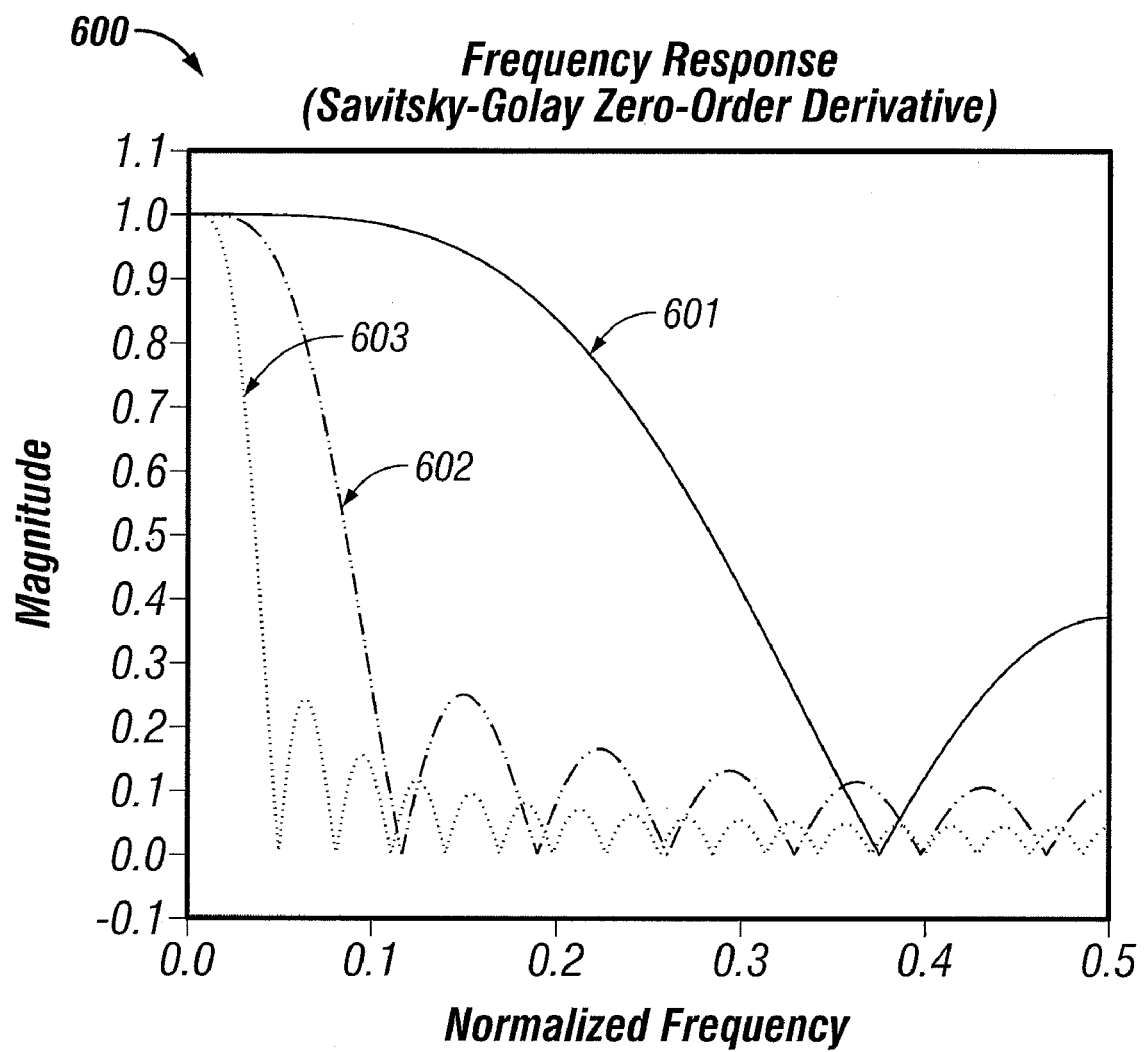
FIG. 7 illustrates the relative filtering of different frequencies using a zero-order derivative.

Referring now to FIG. 7, several examples of zero-order derivative filters 600, presented in frequency space, are provided. The three represented filters are all Savitsky-Golay zero-order derivative filters with 5, 15, and 35-point windows, respectively. The 5-point zero-order derivative filter 601 is observed to have a high response at low frequency and to generally roll off at higher frequency. The response of this filter is to pass low frequency information, such as baseline deviations, and to remove some high frequency information from the spectra, such as noise. The 15-point zero-order derivative filter 602 again passes very low frequency information but has a much steeper roll-off. The steeper roll off results in a greater percentage removal of semi-high frequency noise. Notably, the filter rings at higher frequency. Each of the local maxima at higher frequency result in some high frequency noise being passed by the filter. These local maxima are referred to as leaks in the filter. The 35-point zero-order derivative filter 603 again passes low frequency information and has a sharper cut-off. Generally, a zero-order derivative filter passes low frequency information, reduces high-frequency information, has a steeper negative slope with an increasing number of points, and leaks some high frequency response. All of these filters leak high-frequency noise and defining two points of a filter defines the magnitude at all frequencies for a given filter.

Figure 8:
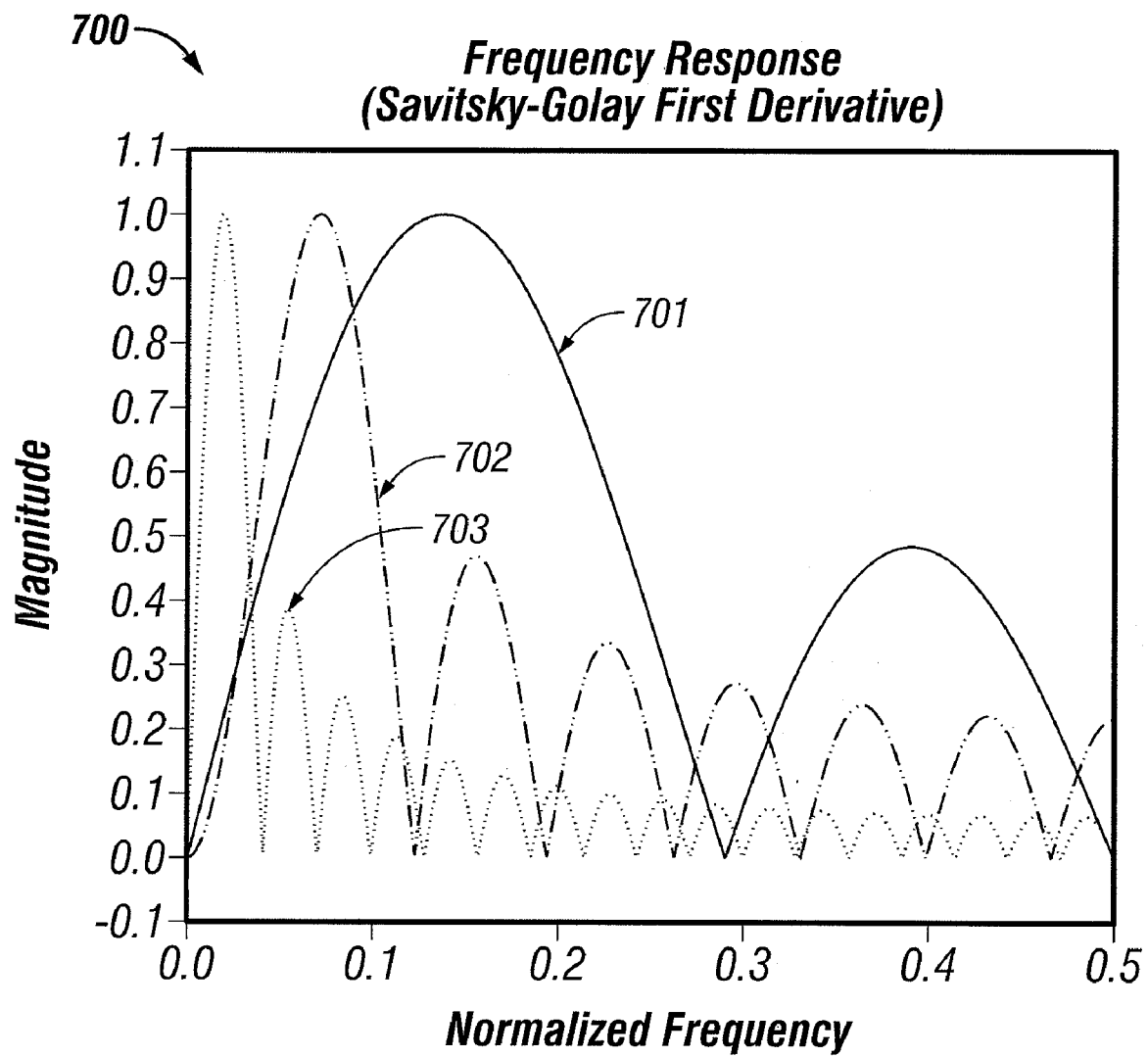
FIG. 8 illustrates the relative filtering of different frequencies using a first order derivative.

Referring now to FIG. 8, several examples of first-order derivative filters 700, presented in frequency space, are provided. The three represented filters are all Savitsky-Golay first-derivative filters with 5, 15, and 35-point windows, respectively. The 5-point first-order derivative filter 701 strongly attenuates very low frequencies, is observed to have a peak response at a low-frequency, again attenuates to a degree at higher frequency, and has ripple at still greater frequency. The response of this filter is thus to attenuate very low frequency information greatly, such as baseline deviations, to pass low-frequency, and to again greatly attenuate high frequency noise with secondary ripple passing high frequency noise. The 15-point first-order derivative filter 702 attenuates very low frequency information but has a narrower passband at lower frequency than the 5-point first-order derivative filter, and more ripples leaking high frequency noise. The 35-point first-order derivative filter 703 attenuates to a degree low and high-frequency information, has a passband at relatively lower frequency, and has many ripples leaking higher frequency information, such as high-frequency noise. Generally, a first-order derivative filter filters both high and low frequency information, has a passband that passes narrower regions at lower frequencies with an increase in the number of filter points in the convolution, leaks high frequency response through the ripples of the filter, and has a low degree of freedom.

Figure 9:
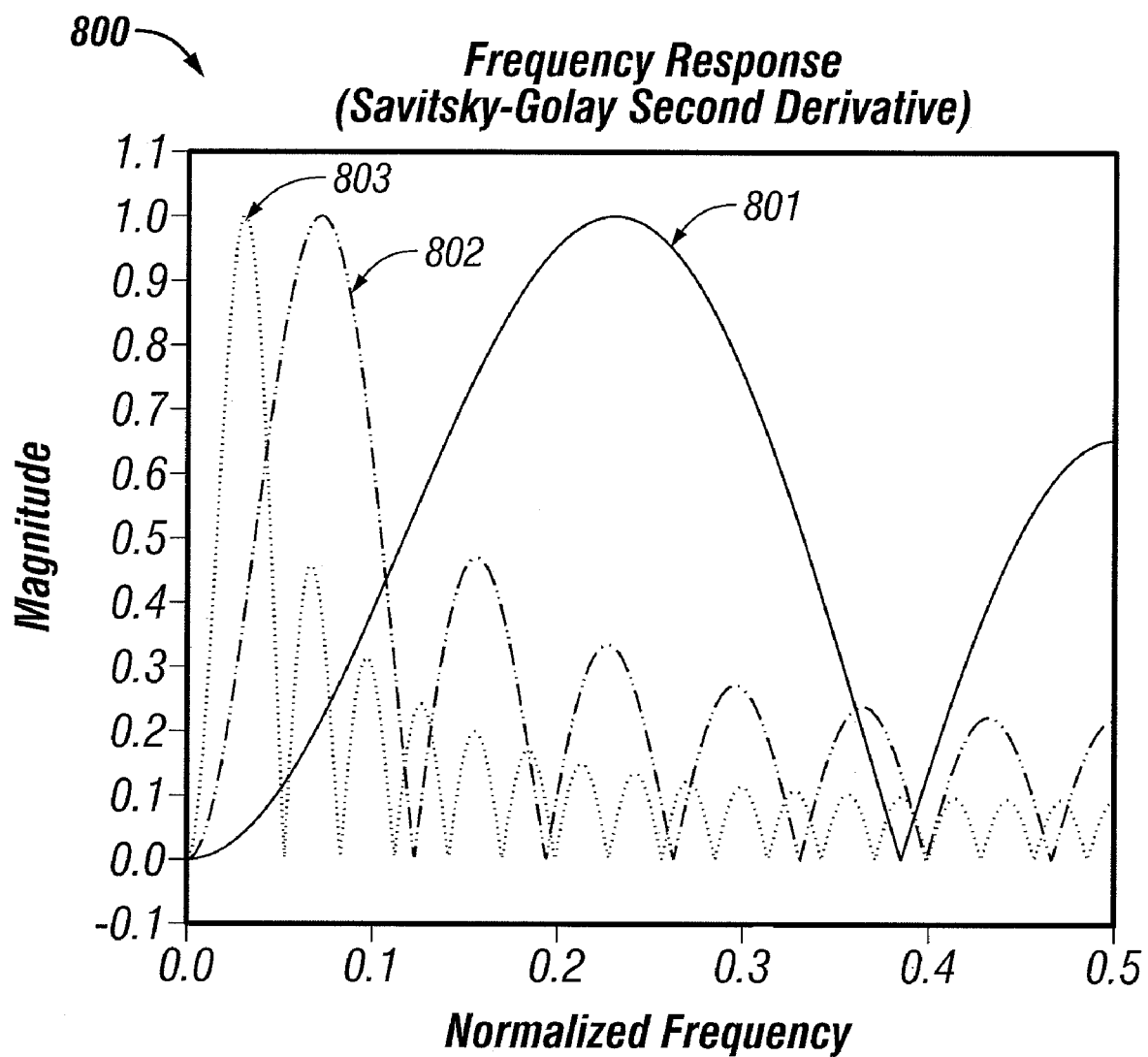
FIG. 9 illustrates the relative filtering of different frequencies using a second order derivative.

Referring now to FIG. 9, several examples of second-order derivative filters 800, presented in frequency space, are provided. The three represented filters are all Savitsky-Golay second-derivative filters with 5, 15, and 35-point windows, respectively. The 5-point second-derivative filter 801 greatly attenuates low frequency, is observed to have a peak response at an intermediate frequency, again attenuates to a degree at higher frequency, and has ripple at still greater frequency. Thus, the response of this filter is to attenuate low frequency information greatly, such as baseline deviations, to pass intermediate-frequency, and to attenuate high frequency noise somewhat with secondary ripple passing high frequency noise. The 15-point second derivative filter 802 again greatly attenuates very low frequency information, but has a narrower passband at lower frequency than the 5-point second-derivative filter, and more ripples leaking high frequency noise. The 35-point second derivative filter 803 attenuates low and high-frequency information, has a passband at relatively lower frequency, and has many ripples leaking higher frequency information, such as high-frequency noise. Generally, a second-order derivative filter filters both high and low frequency information, has a passband that passes narrower regions at lower frequency with an increase in the number of filter points in the convolution, leaks high frequency response through the ripples of the filter, and has a low degree of freedom.

Higher order derivative filters have responses that are extended trends from the first and second derivative filters. Generally, a higher order derivative filter filters both high and low frequency information, has a passband that passes narrower regions at lower frequency with an increase in the number of filter points in the convolution, leaks high frequency response through the ripples of the filter, and is restricted in terms of magnitude response across frequency.

Order-filters are restricted in terms of independent magnitude of response versus frequency. For example, if a desired filtering efficiency is set at two frequencies, then an order-filter that achieves this response necessarily has some filtering efficiency at another frequency. For example, forcing a filter to greatly attenuate very low frequencies results in ripples passing higher frequency. As a second example, forcing a narrower bandpass results in a greater number of ripples. The restriction of one shape of the filter by defining another limits performance of the filters. Analyte filters are not limited by these restrictions.

Fourier Filters

Another example of a filter is a Gaussian filter. A Gaussian filter reduces both baseline deviations occurring at low normalized frequency units, reduces high frequency noise occurring at high normalized frequency units, and has a passband over a range of intermediate normalized digital frequency units. A Gaussian function is defined by its mean and standard deviation. This restricts the curvature of the of cut-on and the cut-off of the filter to be symmetrical. This symmetry restricts the flexibility of having a sharper cut-on versus the cut-off or vise versa.

Figure 10:
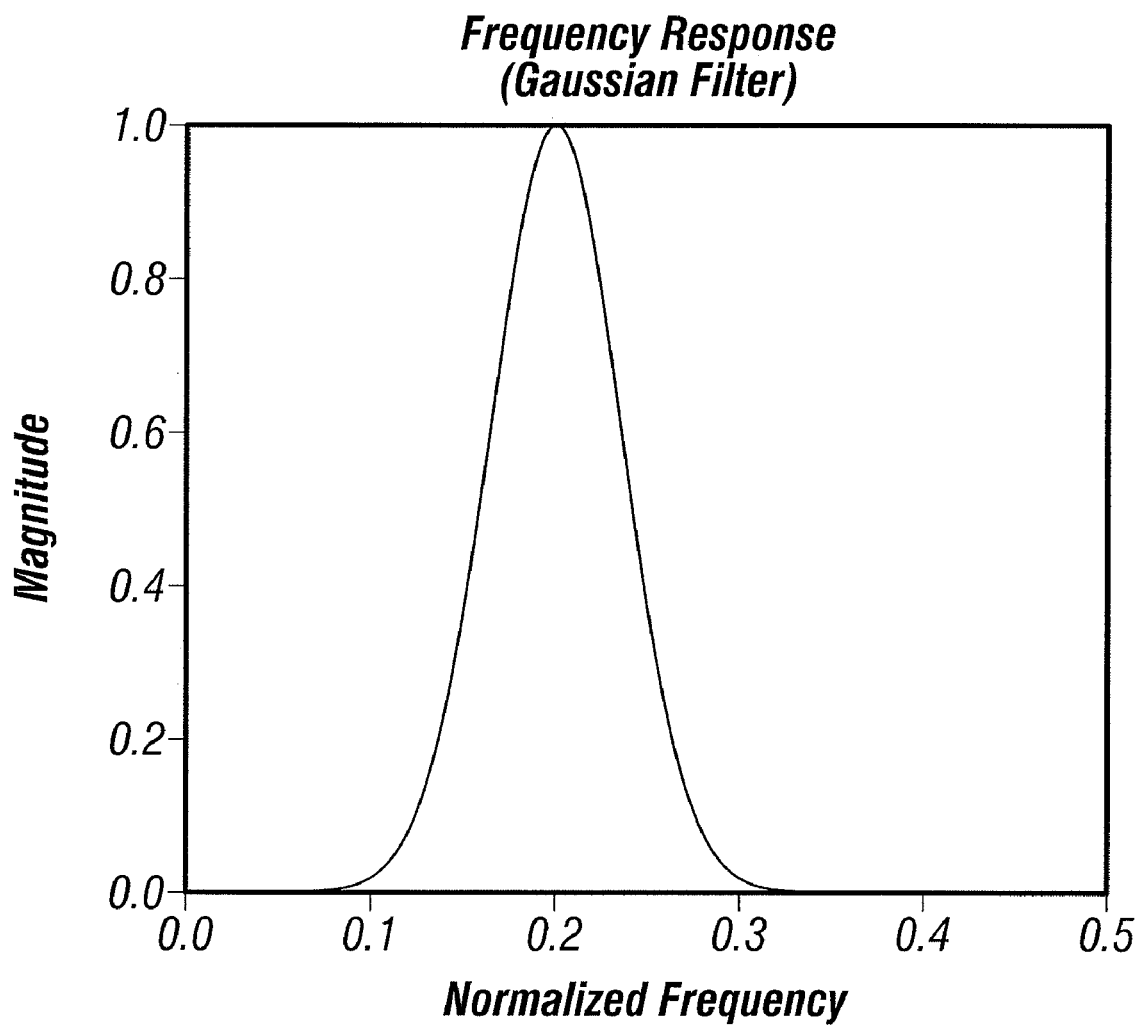
FIG. 10 illustrates the relative filtering of different frequencies using a Gaussian filter.

Referring now to FIG. 10, an example of a Gaussian filter is provided having a mean of 0.2 and a standard deviation of 0.05. Fourier filters operate by performing a Fourier transform of an absorbance spectrum as a function of wavelength to represent the data in intensity versus frequency. The transformed spectrum multiplied by a Gaussian function and an inverse Fourier transform is subsequently performed to transform the spectrum back to its original domain. Again, this Gaussian filter type is constrained as a Gaussian filter is defined by a mean and a standard deviation so that the roll-off of one side of the filter necessarily impacts the roll-off of the opposite side of the filter. A Gaussian filter is restricted. If two points are defined, then the rest of the Gaussian filter shape is defined. The low degree of freedom restriction of shape and/ or symmetry of a Gaussian filter is not present in an analyte filter. This allows the analyte filter to be designed or built based upon the actual frequency response of the analyte in the presence of noise and interference.

Analyte Filters

An analyte filter is a filter that preferably rejects variations that are likely to be detrimental to the measurement system, while passing the signal that is most likely unique to the target analyte. For example, an analyte filter based upon shape information of the target analyte, which is based upon the analyte signal in the presence of noise and/or interference, is represented by the net analyte signal, or is based upon one or more extracted features. A typical use of an analyte filter is to improve the robustness of a calibration with respect to sources of interference. Typically, an analyte filter is built or optimized to a set of specifications that can include: the analyte signal, noise, and interference. Preferably an analyte filter is used in combination with a multivariate soft model, such as partial least square or principal component regression, as soft models have difficulties compensating for noise, baseline variation, and interferences. The analyte filter removes, minimizes, or reduces noise, baseline deviation, and interferences.

To enhance the analyte filter functionality, the analyte filter is optionally implemented in several stages, each stage designed and optimized according to a particular criterion. In one case, an analyte filter is generated or enhanced through a theoretical design that involves the use of interference models, in addition to shape information, to develop an optimized analyte filter. In a second case, an iterative approach is used to generate or enhance an analyte filter shape, where the iterative approach uses knowledge of the analyte and/or noise frequency response of the system. An analyte filter is not restricted in the frequency domain in the manner of a derivative leaking excess high frequency noise, is not restricted to a symmetrical shape, and has an $n^{th}$ point in the frequency domain not restricted by a combination of two, three, four, five or more points of the analyte filter in the frequency domain.

Based upon the specification and/or design approach of an analyte filter, a number of approaches are used to generate an analyte filter for an application. Several example processes of analyte filter design are provided, infra.

EXAMPLE II

Shape Based Design

An analyte filter is optionally created or optimized using the shape of the target analyte, preferably in conjunction with interference. The pure component spectrum of a target analyte is often considered the signal of interest in applications involving spectroscopy and noninvasive analyte property determination. The use of preprocessing techniques is traditionally aimed at enhancing and extracting the pure component analyte signal. However, the true signal of interest in multivariate applications is contained in the shape of the target analyte after orthogonalization with respect to the interference. Specifically, the net analyte signal defines that portion of the pure component analyte spectrum that is accessible for analyte measurement and is often significantly different than the pure component spectrum related to the target analyte.

Therefore, shape is the signal in the presence of interference. One measure of signal strength is the net analyte signal, nas, given by the projection of the pure component analyte signal, R, onto the null space of the interference contained in the B, where I is the identity matrix as provided in equation 1.

$$nas = [I - BB^+]R. \quad (1)$$

The interference, B, is a basis set that spans at least a portion of the space of expected variation. Alternately, nas is estimated from the regression vector of the multivariate calibration.

The net analyte signal constitutes a pattern, contained in the vector nas, with shape information that is used to determine the optimal filter characteristics. The frequency response of the nas, denoted nas(f), provides the magnitude and phase of the signal of interest versus the normalized frequency and is used to establish filter criteria yielding minimal attenuation of the signal of interest. In particular, a filter is designed to pass frequency components of the nas that are significant while rejecting harmonics that contribute minimally to the analyte property estimation.

Several applicable cases of the invention are provided as exemplar embodiments. In one case, a primary interference affecting the analyte measurement is related to low frequency harmonics that develop due to instrument drift, instrument-to-instrument differences, and/or gross changes in the scattering properties of the tissue between subjects and over time. The enhancement of analytical signal, optionally measured by the nas, is performed by rejecting low frequency interference and passing frequency components that has the highest probability of representing the signal of interest in subsequent samples.

Therefore, a high-pass filter is implemented with a break frequency or cut-on, $f_c$, that is established on the basis of nas(f). The selection of break frequency is based upon the point at which |nas(f)| falls below a minimum threshold level, which is typically about an order of magnitude less than the maximum frequency component though of fractional order of magnitude or two or more orders of magnitude less thresholds is optionally used.

In addition, specific features of the analyte signal, the signal in the presence of interference, or the nas are extracted to provide further information to enhance the design of the analyte filter. For example, the most influential regions of the nas are characterized according to wavelength range, frequency content, and bandwidth. Optionally, these features are extracted using preprocessing techniques, described infra. Optimal filters are employed as a function of the influential individual regions yielding a net improvement in the analyte performance.

EXAMPLE III

Theoretical Design

In another embodiment of the invention, a-priori knowledge of the measured system is used in the creation and/or optimization of an analyte filter. The use of a-priori knowledge for the development of an analyte filter is accomplished by selecting, parameterizing, and implementing an optimized filter using what is known about noise, interference, and the signal of interest. This method does not directly rely on a set of empirical data for the determination of the analyte filter, but instead uses theoretical methods to make a robust and optimal system for separating the spectroscopic signal from noise and interference. Optionally, a-priori knowledge is used in conjunction with, subsequent to, concurrently with, or iteratively with empirical data in analyte filter creation.

The a-prior information about random noise is in the form of one or more models, such as a statistical model, that are used to provide the corresponding frequency characteristics, N(f). For example, the a-priori information about interfering analytes is provided through an estimate of the net analyte signal, extracted features, interferences, and/or noise characteristics, which provide shape information about the signal of interest. A-priori knowledge in analyte filter design is optionally used in combination with preprocessing.

There are two fundamental steps for the theoretical design. First, the low frequency variation over the wavelength axis of the measured spectrum is attenuated through a high-pass filtering operation. The cut-off frequency or bandwidth of the high-pass operation is determined according to the shape information of the nas as previously discussed. The second function is a low-pass or smoothing operation in which noise is suppressed through the attenuation of high frequencies. The break frequency of the low-pass filter is set according to the bandwidth of the spectrometer, the net analyte signal of the target analyte or constituent, and/or the necessary signal-to-noise ratio required to make the measurement. For example, a-priori knowledge of the system is used to generate a two-stage filter.

In one embodiment of the invention, the measured spectrum is oversampled with respect to the wavelength axis and the low-pass bandwidth is set based upon an analysis of the signal-to-noise ratio where the net analyte signal is the signal and the noise is the root-mean-square variation of the measured spectrum in the wavelength region used for measurement of the target analyte. As the low-pass bandwidth is reduced, the high frequency components of the noise are attenuated, leading to a reduction in the root-mean-square noise. However, this process also attenuates the high frequency components of the signal leading to a simultaneous reduction in the net analyte signal. In cases in which the spectrum is oversampled with respect to the wavelength axis, the noise is distributed in greater proportions at higher frequencies than the net analyte signal. Therefore, low-pass filtering the measured spectrum removes a greater proportion of the noise than the net analyte signal. The optimal low-pass bandwidth can be defined as one that maximizes the ratio of the signal or net analyte signal to the noise. Given a frequency domain model the net analyte signal, NAS(f), and the noise, N(f), the bandwidth of the low-pass filter, $f_{bw}$, can be determined through equation 2

$$SNR(f_{bw})^2 = \frac{\sum_{f=0}^{f_{bw}} |NAS(f)|^2}{\sum_{f=0}^{f_{bw}} |N(f)|^2} \quad (2)$$

as the value for $f_{bw}$ at which $SNR(f_{bw})$ is maximized. Alternately, this can be performed iteratively by filtering a wavelength domain representation of the net analyte signal and noise at various low-pass bandwidths, or through an empirical set of data by selecting the break frequency to optimize the standard error of prediction or other figure of merit. The break frequency of the high-pass section is set to attenuate low frequency variation caused by changes in the scattering while passing the net analyte signal. This is generally accomplished empirically through an exemplary set of data or through a harmonic analysis of the net analyte signal. Optionally, signal as opposed to net analyte signal is used in this optimization.

In an alternate embodiment, the analyte filter is employed to compensate for instrument related shape distortion that causes a contraction, dilation, or shift. For example, a-prior knowledge of wavelengths of absorbance of a particular feature are optionally used as standards for a wavelength correction. In terms of an analyte filter used to adjust shift distortion, a Bessel-Thomson filter is used to provide a constant correction with respect to wavelength. The measurement of a complete spectrum enables that filter to be either causal or non-causal, which provide the opportunity to shift a spectrum in either direction along an axis. Alternatively, complex structures or adaptive means are employed for adjusting the filter characteristics on the basis of an acquired signal representative of the distortion. Adaptive means for filtering using wavelets, artificial neural networks, a Kalman filter, and related methods are also used, depending on the application.

EXAMPLE IV

Array Based

Figure 11:
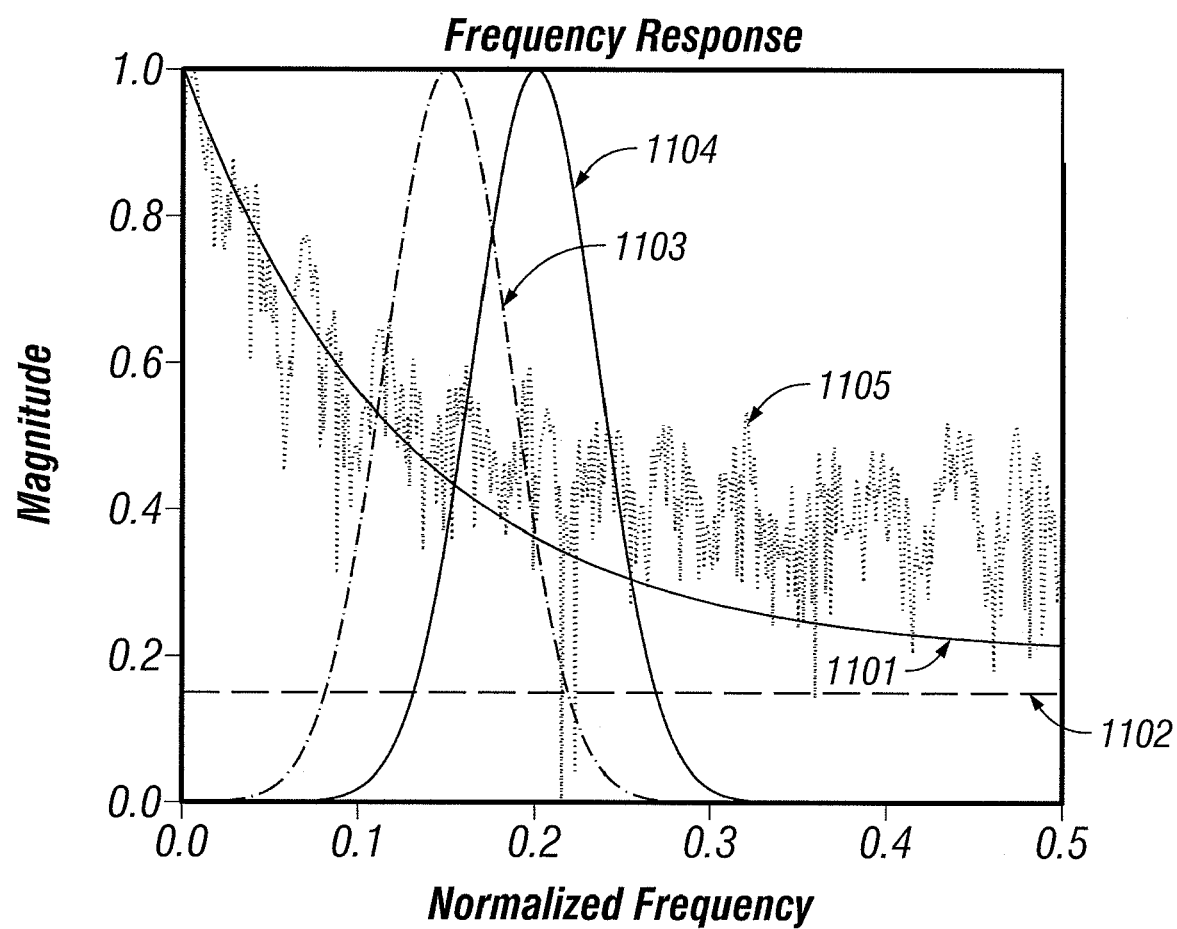
FIG. 11 illustrates benefits of an analyte filter in terms of signal and noise.

In another embodiment of the invention, an analyte filter is used to take advantage of known hardware features. For example, many existing spectrometer systems use a single element detector as a means for generating a response, such as a near-infrared spectrum. A principle problem with this approach is that the serial extraction of intensity over time leads to a wavelength-to-wavelength correlation in the noise. Consequently, the frequency response of the measurement noise is dominated by low-frequency harmonics that can not be efficiently filtered without also attenuating the signal of interest. For this reason, an array-based system is employed, where a multiplicity of detectors convert spatially distributed electromagnetic energy into a spectrum suitable for processing. Each element detects a band of wavelengths and operates independently. It is determined that because the detectors are independent, the noise versus wavelength is white and the frequency response is flat, enabling a highly efficient reduction of noise through filtering. Hence, an analyte filter optimized for the same matrix with the same chemical and environment interferences is different for an array based spectrometer and a single element detector based spectrometer. Most analytes in visible, near-infrared, or infrared spectroscopy are dominated by low frequencies. For instance, referring now to FIG. 11, a single element detector is characterized by an increasing magnitude of noise as the normalized frequency decreases 1101. In stark contrast, the frequency response of an array detector is flat or nearly flat 1102. This means that the lower frequency noise of the array detector is de-emphasized. As a result, an analyte filter optimized for a glucose signal using an array detector optimally shifts to lower frequencies 1103, compared to an analyte filter optimized for a glucose signal using a single element detector 1104. Typically, molecular analytes have spectral signatures dominated by lower frequencies. A near-infrared glucose signal in frequency space 1105 exemplifies this. Accordingly, the analyte filter optimized using the flat noise characteristic moves closer to the low frequencies that dominate the glucose signal. Hence, the analyte filter generated using an array detector is different and more efficient compared to the analyte filter optimized for the glucose signal using a single element detector. The lower frequency analyte filter optimized with a detector array noise structure allows extraction of a greater portion of the glucose signal, resulting in improved performance of the analyte concentration estimation using noninvasive spectra.

EXAMPLE V

Cluster/Analyte Filter

When spectral interference is significant as a result of the heterogeneity, a dynamic nature of the measurement site, and/or instrument performance state or characteristics, it is beneficial to develop an analyte filter associated with a particular cluster of samples that represent a more uniform tissue state. In this particular circumstance, the analyte filter is preferably associated with a particular calibration that is specific to the variation represented by the cluster.

For this purpose we disclose an adaptive filter that, in addition to the more general analyte filter, removes or attenuates spectral interference that is present in a particular cluster. The filter operates by using a basis set of background spectra, such as interference spectra, to reduce the contribution of the cluster specific interference to future measurements.

Herein, a data set is used for calibration including $x_c \in \Re^{P \times N}$ and $y_c \in \Re^{P \times 1}$, where $x_c$ is the matrix of tissue measurements, $y_c$ is a vector of analyte concentrations, P is sample number, and N is data point, such as wavelength, where $x_c$ and $y_c$ are collected or associated with a particular state. A state is defined by one or more of the following: subject, day, time, tissue position, temperature, environmental condition, tissue properties, instrument state, etc. During calibration it is often advantageous to combine data associated with multiple states so that a more certain estimate of the analyte signal relative to noise is determined. However, the different states often result in highly nonlinear variation that is difficult to model. The adaptive filter uses a set of background spectra, which define the interference to optimally reduce subsequent contributions of similarly shaped interference.

The filter operates according to equation 3

$$x'_c = x_c [I - x_b^T (x_b^T)^{-1}] \tag{3}$$

where the basis set spectra, $x_b$, the pseudo inverse, $(x_b^T)^{-1}$, and the measured spectrum, $x_c$, are used to the corrected spectrum or analyte filtered spectrum, $x_c'$, and equation 4

$$y'_c = y_c - \frac{1}{L} \sum_{k=1}^{L} y_{c,k} \tag{4}$$

where $y_c$ is the reference concentration, the $k^{th}$ element of $y_c$ is, $y_{c,k}$, and L is the set of spectra used to calculated $x_b$. During the process of measurement, a basis set is determined using the first one or more spectra associated with a particular condition. Subsequent samples are adaptively filtered using the method above until a change in the interference is detected.

The analyte filter is used to adapt a spectral reading to a nearest cluster, to translate a reading from one cluster to another cluster, and to determine outliers as described in U.S. patent application Ser. No. 09/664,973 filed Sep. 18, 2000 and in U.S. patent application Ser. No. 10/870,727 filed Jun. 16, 2004 both of which are incorporated herein in their entirety by this reference thereto.

EXAMPLE VI

Multi-Stage Filter

An analyte filter is optionally designed to the signal of interest compensating for noise structure without restraint on the analyte filter shape. Existing filter methodologies for non-invasive detection of analytes are limited as a consequence of the underlying filter structure. Although the design of the optimal analyte filter involves the use of multiple design goals, existing filter implementations constrain the high-pass and low-pass filter characteristics according to a deterministic function. For example, filtering involves the use of functions, such as the Savitsky-Golay derivative, which contain significant stop-band ripple and thereby pass unwanted noise. Passing unwanted high frequency noise results in performance degradation, as described supra. For example, a finite-impulse response filter is designed and implemented by constraining the frequency response according to a Gaussian curve. While the resulting step response with respect to the wavelength axis is well behaved, the low and high-pass filter characteristics are necessarily sub-optimal due to symmetry restrictions. In a second example, other methods of filtering involve the use of functions, such as the Savitsky-Golay derivative, which contain significant stop-band ripple and thereby pass unwanted noise, which leads to performance degradations.

In yet another embodiment of the invention, the problems of a restrained filter or a filter leaking excess high frequency noise are addressed. The generation of a filter that is optimized according to the shape information contained in the signal of the analyte, such as the net analyte signal, and the noise is preferably performed with at least two design goals and involves a stage for each goal. For example, optimization of the signal is preferably performed with optimization of a longpass filter or with a highpass filter designed to pass the signal or net analyte signal frequency response shape. Before or after optimization of the signal, a filter is optimized for the noise structure. For example, a shortpass or lowpass filter is used or optimized based upon the noise structure so that high frequency noise is reduced, minimized, or eliminated. The signal and noise optimization functions are optionally performed in either order depending on the implementation of the band-pass filter. The methods used for performing this operation include infinite-impulse response (IIR) and finite-impulse response (FIR) band-pass filtering. In the preferred embodiment a FIR filter is implemented according to equation 5, $$m_{f,j} = \sum_{k=1}^{P} a_k m_{j-k-(p-1)/2} \tag{5}$$

where $m_{f,j}$ is the filtered spectrum at the $j^{th}$ measured wavelength, $m_j$ is the measured spectrum at the $j^{th}$ wavelength, $a_k$ denotes the $k^{th}$ filter coefficient and P is the length of the filter impulse response or filter window width. In equation 5, the filter is non-causal and applied across the wavelength axis of the measured spectrum. The filter width, P, is assumed to be an odd number and the filter coefficients are determined according to the desired filter break frequencies and characteristics of the pass and stop-bands. This multiple stage filter approach reduces and in some instances eliminates the restraints of traditional filters.

EXAMPLE VII

Analyte filters are optionally built based upon specifications and/or shape. For example, combinations of longpass, shortpass and Butterworth filters are used to meet objectives set out in the specification requirements of a given design filter. Combinations of filters are created resulting in a complex filter, a two-stage filter, a three stage-filter, or an $n^{th}$ stage filter.

The concern of restriction of filter shape, such as with the Gaussian filters, and the concern of excessive high frequency leaking of a filter, such as with derivative filters, is avoided with non-symmetrical filters, such as shortpass filters, longpass filters, bandpass or passband filters, and IIR Butterworth filters. However, these filter types are not customarily used in combination to create an analyte filter shape based upon a set of specifications. Combinations of these filters minimize high frequency leaking, reduce baseline deviation, avoid symmetry concerns, and match, correlate, or correspond to the specified shape of the analyte frequency response in the presence of interference. In tuning the combination filters to the shape of the analyte response, the order of the filters, such as the longpass filter, or shortpass filter, is varied.

Herein, a complex filter has a simple or complex shape. In general, complex filters are not restricted to the limitations of an order derivative filter or a Gaussian filter. For example, the filters need not be symmetrical and do not necessarily pass higher frequency intensity noise. A complex filter is generated in many ways. For example, a complex filter is optimized using a response function, theoretically generated using net analyte signal, designed for noise reduction, or is a complex shape designed from multiple inputs.

EXAMPLE VIII

Calibration Transfer

In still yet another embodiment of the invention, an analyte filter is generated using data from a first set of analyzers or spectrometers. An additional analyzer or a second set of analyzers that are not present in the first set of analyzers have distinct spectral characteristics that can degrade analytical performance of analyte property determination. Implementation of a model built on the first set of analyzers onto the second set of analyzers thus requires a calibration transfer or filter for optimal performance.

Overview

Calibration transfer is a standardization procedure designed to eliminate a full recalibration and to maintain information residing in the existing model. Calibration transfer is useful because in the development of the training set, also referred to as a calibration set, sources of variation in the instrument, sample, and environment are modeled. Therefore, as the instrument, sample, or environment state changes the model components do not exactly match the current state. These problems are typically compounded when transferring a calibration from a first spectrometer to a second spectrometer. Calibration transfer addresses a range of concerns including: wavelength or x-axis stability, energy throughput or y-axis stability, and bandwidth. Calibration transfers are used across time on one or more instruments, across many instruments of the same design, and across instruments of different design. Calibration transfer is also used when the sample varies. A living organism, such as the human body, undergoes continuous change. In addition, calibration transfers are used to adjust for changes in the environmental conditions, such as changes in humidity or temperature. While broad models account for many changes, changing state still leads to an increase in estimation error or analyte determination.

Sources of Variation

There are many potential sources of variation in an optical based analyzers, which are referred to herein as spectrometers or analyzers.

A first source of variation is when there is a change in the entire spectrometer design. This is the case, for example, when a calibration is built on a first spectrometer, such as a master spectrometer and estimations or predictions are performed on a different spectrometer, such as a slave spectrometer. This first type of variation is common when a research grade spectrometer is used for calibration and a process grade spectrometer, built with less stringent specifications, is used for subsequent analyses.

A second source of variation is a change in a part of a spectrometer. Examples of changing a part of a spectrometer include: changing a source, which can effect the blackbody radiation emitted; changing a monochromator or grating, which can effect the wavelength axis; changing a fiber optic or fiber bundle, which can effect the bandwidth; or changing the detector, which can effect the response curve or change a high or low frequency cut-off.

A third source of variation results from alignment of the spectrometer. Alignment changes result from movement of one or more of sub-components of the spectrometer. Alignment issues also result from mechanical design and fabrication tolerances.

A fourth source of variation is change in the environmental conditions about the spectrometer or analyzer. Common environmental changes affecting near-infrared spectra include temperature and humidity.

A fifth source of variation is a change in the sample. Examples of changes in the sample include changes in chemical composition, sample finish, particle size distribution, and density. Examples of changes in a skin sample include changes in temperature, chemical composition, chemical distribution, physical structure, hydration, and/or localized pressure.

In its broadest sense, the state of the spectrometer affects its output. Variation in state results in variation of output. For example, variation in state results in variation of the observed or calculated absorption coefficient and/or the observed or calculated reduced scattering coefficient. Calibration transfer is useful for adjusting for or compensating for the change in output resulting from change in state.

Techniques

As described, supra, identical performance of analytical instruments is unrealistic even with the successful implementation of tight quality control on instrument hardware. For example, variation in the output of a source, quality of lenses or mirrors, alignment, and detector response, which are limited by manufacturing tolerances, result in differences between spectrometers even of the same design. The instrument differences result in spectra of the master instrument varying from that of the slave instrument. Variations between the spectrometers result in errors when using a calibration developed on a spectrometer to determine parameters with a second spectrometer. Generally, this error is increasingly detrimental as the signal-to-noise ratio of the determined analyte decreases.

Existing techniques, such as developing a robust model that covers all future conditions, full recalibration of an analyzer, and axis standardization using a standard are limited in terms of breadth of use, time and cost, and effectiveness. Herein an analyte filter is used advantageously in the calibration transfer process. The analyte filter is used to extract the signal from a known type of interference or from a particular cluster of sample as provided herein. The analyte filter is optionally used with a preprocessing and/or processing step. Several preprocessing techniques are described, infra.

Preprocessing

In data preprocessing, typically the same preprocessing is performed on data that are used to generate a calibration model and the data that the model applied to. Generally, these techniques modify spectral response, such that spectra collected on different instruments are transformed so that the spectra appear as though they were all measured on the same instrument. However, identical preprocessing is not necessary. Preprocessing techniques include: multiplicative scatter correction, standard normal variate transformation, finite impulse response, a Bessel filter, normalization, a moving average, a finite impulse response filter, an infinite impulse response filter, and Fourier transformation. An additional preprocessing technique is extraction of an absorbance and/or scattering signal with one or more sub-ranges of a spectrum. The selected and optionally further modified signal is preferably subsequently filtered with an analyte filter.

Although the invention is described herein with reference to the preferred embodiments, one skilled in the art will readily appreciate that other applications may be substituted for those set forth herein without departing from the spirit and scope of the present invention. Accordingly, the invention should only be limited by the claims included below.

The invention claimed is:

1. A method for determining a property of an analyte using a noninvasive spectrum, comprising the steps of:
processing said noninvasive spectrum using an analyte filter yielding a processed spectrum, wherein said analyte filter correlates with frequency response shape of said analyte;
generating said analyte filter using a set of spectra from a first set of spectrometers; and
estimating said property using a multivariate model and said processed spectrum.

2. The method of claim 1, further comprising the step of:
extracting a feature representative of said response shape of said analyte in frequency response.

3. The method of claim 2, wherein said analyte filter enhances said shape in frequency response below a break frequency.

4. The method of claim 3, wherein said analyte filter enhances said shape in frequency responses above a break frequency.

5. The method of claim 2, wherein said feature is characterized in terms of signal and interference.

6. The method of claim 1, wherein said multivariate model comprises any of:
principal component regression; and
partial least squares.

7. The method of claim 1, wherein said frequency response shape of said analyte comprises any of:
a net analyte signal;
an accessible portion of a pure component analyte spectrum; and
shape of said analyte after orthogonalization with respect to interference.

8. The method of claim 7, further comprising the step of:
calculating said shape of said net analyte signal according to:

$$nas = [I - BB^+]R$$

wherein said net analyte signal, nas, is given by the projection of the pure component analyte signal, R, onto the null space of the interference contained in B, wherein B is a basis set that spans at least a portion of the space of expected variation and I is the identity matrix.

9. The method of claim 7, further comprising the step of:
estimating said net analyte signal from a regression vector of said multivariate model.

10. The method of claim 1, further comprising the step of:
theoretically generating said analyte filter using frequency response shape of said analyte.

11. The method of claim 10, wherein said step of theoretically generating further comprises the steps of:
applying a-priori knowledge of signal of a system from which said noninvasive spectrum is collected; and
applying a-priori knowledge of interference of said system from which said noninvasive spectrum is collected.

12. The method of claim 11, wherein said step of theoretically generating further comprises the step of:
generating a multi-stage filter.

13. The method of claim 12, wherein said multi-stage filter comprises:
a two-stage filter.

14. The method of claim 13, wherein said two-stage filter comprises:
a lowpass filter; and
a highpass filter.

15. The method of claim 1, further comprising the step of:
preprocessing said noninvasive spectrum prior to said step of processing, wherein preprocessing enhances at least a portion of said shape of said analyte.

16. The method of claim 10, further comprising the step of:
iteratively generating frequency response of said analyte filter.

17. The method of claim 16, wherein said steps of theoretically generating and iteratively generating comprise any of:
sequential performance;
concurrent performance; and
iterative performance.

18. The method of claim 1, further comprising the step of:
iteratively generating frequency response shape of said analyte filter using a set of data from a first set of spectrometers; and
implementing said analyte filter on a second spectrometer, wherein said second spectrometer is not a member of said first set of spectrometers.

19. The method of claim 1, further comprising the step of:
implementing said analyte filter on at least one spectrum from a second set of spectrometers, wherein a union of said first set of spectrometers and said second set of spectrometers results in an empty set.

20. The method of claim 19, wherein said step of estimating further comprises the step of:
performing multivariate analysis.

21. The method of claim 20, where said step of performing multivariate analysis comprises use of any of:
a regression model;
partial least squares; and
a principal component regression.

22. The method of claim 1, wherein said analyte filter comprises an $n^{th}$ point in the frequency domain not restricted by said analyte filter points at a combination of a first, a second, a third, and/or a fourth point of the analyte filter in the frequency domain.

23. The method of claim 1, wherein said analyte filter comprises:
   a cluster filter.

24. The method of claim 23, further comprising any of the steps of:
   attenuating spectral interference present in a cluster; and
   removing spectral interference present in said cluster.

25. The method of claim 24, wherein said cluster filter facilitates calibration transfer of said noninvasive spectrum.

26. The method of claim 24, wherein said cluster filter compensates for variation in any of:
   a sample;
   an analyzer; and
   an environmental state.

27. The method of claim 24, wherein said multivariate model is associated with said cluster.

28. The method of claim 24, wherein said cluster filter compensates for variation of:
   a subject;
   a sampling position;
   temperature; and
   instrument state.

29. The method of claim 25, wherein said cluster filter operates according to:

$$y'_c = y_c - \frac{1}{L}\sum_{k=1}^{L} y_{c,k}$$

wherein $y_c$ is a reference concentration, a $k^{th}$ element of $y_c$ is $y_{c,k}$, and L is a set of spectra used to calculate $y'_c$.

30. The method of claim 1, wherein said analyte filter comprises a product of a derivative order filter and a shortpass filter, wherein high frequency noise leaked by said derivative order filter is reduced.

31. The method of claim 1, further comprising the step of:
   developing said analyte filter using said analyte property shape.

32. The method of claim 31, further comprising the step of:
   using interference of said analyte in said step of developing said analyte filter.

33. The method of claim 1, wherein said analyte filter comprises a multi-stage filter.

34. The method of claim 33, wherein said multi-stage filter comprises a two-stage filter.

35. The method of claim 1, wherein said noninvasive spectrum comprises:
   a near-infrared spectrum; at least a portion of said near-infrared spectrum being in the range 1150 to 1850 nm.

36. The method of claim 35, wherein said analyte property comprises:
   a glucose concentration.

37. The method of claim 36, further comprising the step of:
   generating said noninvasive spectrum using a photo diode array detector.

38. The method of claim 37, further comprising the step of:
   implementing said analyte filter on an analyzer not used to develop said analyte filter.

39. An apparatus for determining an analyte property using a noninvasive spectrum, comprising:
   means for obtaining said noninvasive spectrum; and
   an analyzer, comprising:
      a processor;
      an algorithm executed by said processor;
      an analyte filter operating as a step in said algorithm; and
      a multivariate model operating as a step in said algorithm,
   said analyzer operating on said noninvasive spectrum using said analyte filter to yield a processed spectrum;
   said analyte filter correlating with frequency response shape of said analyte; and
   said multivariate model operating on said processed spectrum to yield said analyte property;
   wherein said analyte filter is generated using a set of data from a set of spectrometers, wherein said analyzer is not a member of said set of spectrometers.

40. The apparatus of claim 39, wherein said shape comprises an extracted feature of said analyte in frequency response.

41. The apparatus of claim 40, wherein said algorithm further comprises:
   preprocessing means for extracting said shape of said analyte.

42. The apparatus of claim 39, wherein said analyte filter enhances shape in frequency response below a break frequency.

43. The apparatus of claim 42, wherein said analyte filter enhances shape in frequency responses above a break frequency.

44. The apparatus of claim 40, wherein said extracted feature is characterized in terms of signal and interference.

45. The apparatus of claim 39, wherein said frequency response shape of said analyte comprises any of:
   a net analyte signal;
   an accessible portion of a pure component analyte spectrum; and
   shape of said analyte after orthogonalization with respect to interference.

46. The apparatus of claim 45, wherein said shape comprises said net analyte signal according to:

$$nas = \lfloor I - BB^+ \rfloor R$$

wherein said net analyte signal, nas, is given by the projection of the pure component analyte signal, R, onto the null space of the interference contained in B, wherein B is a basis set that spans at least a portion of the space of expected variation and I is the identity matrix.

47. The apparatus of claim 45, wherein said net analyte signal is estimated from a regression vector of said multivariate model.

48. The apparatus of claim 39, wherein said analyte filter comprises:
   a theoretically generated filter using frequency response shape of said analyte.

49. The apparatus of claim 48, wherein said theoretically generated filter uses:
   a-priori knowledge of signal of a system from which said noninvasive spectrum is collected; and
   a-priori knowledge of interference of said system from which said noninvasive spectrum is collected.

50. The apparatus of claim 49, wherein said theoretically generated filter comprises:
   a multi-stage filter.

51. The apparatus of claim 50, wherein said multi-stage filter comprises:
   a two-stage filter.

52. The apparatus of claim 51, wherein said two-stage filter comprises:
a lowpass filter; and
a highpass filter.
53. The apparatus of claim 51, wherein said algorithm further comprises:
means for preprocessing said noninvasive spectrum prior to said step of processing.
54. The apparatus of claim 48, wherein said analyte filter is iteratively generated using frequency response shape of said analyte.
55. The apparatus of claim 39, where said multivariate model comprises any of:
a regression model;
partial least squares; and
principal component regression.
56. The apparatus of claim 39, wherein said analyte filter comprises an $n^{th}$ point in the frequency domain not restricted by said analyte filter points at a combination of a first, a second, a third, and/or a fourth point of the analyte filter in the frequency domain.
57. The apparatus of claim 39, wherein said analyte filter comprises:
a cluster filter.
58. The apparatus of claim 57, wherein said cluster filter either removes spectral interference or attenuates spectral interference present in a cluster.
59. The apparatus of claim 57, wherein said cluster filter facilitates calibration transfer of said noninvasive spectrum.
60. The apparatus of claim 57, wherein said cluster filter is used to compensate for variation in any of:
a sample;
a subject;
a sampling position;
temperature;
instrument state;
an analyzer; and
an environmental state.
61. The apparatus of claim 57, wherein multivariate model is associated with said cluster filter.
62. The apparatus of claim 57, wherein said cluster filter operates according to:

$$x_c' = x_c \lfloor I - x_b^T (x_b^T)^{-1} \rfloor$$

wherein a basis set spectra, $x_b$, a pseudo inverse, $(x_b^T)^{-1}$, and a measured spectrum, $x_c$, are used to generate a corrected noninvasive spectrum, $x_c'$.
63. The apparatus of claim 62, wherein said cluster filter operates according to:

$$y_c' = y_c - \frac{1}{L} \sum_{k=1}^{L} y_{c,k}$$

wherein $y_c$ is a reference concentration, a $k^{th}$ element of $y_c$ is, $y_{c,k}$, and L is a set of spectra used to calculated $x_b$.
64. The apparatus of claim 39, wherein said analyte filter comprises:
a product of a derivative order filter and a shortpass filter, wherein high frequency noise leaked by said derivative order filter is reduced.
65. The apparatus of claim 39, further comprising:
a photo diode array detector.
66. The apparatus of claim 39, wherein said analyte filter is optimized using said shape.
67. The apparatus of claim 60, wherein said shape comprises:
a roll-on frequency;
a roll-off frequency;
signal; and
noise.
68. The apparatus of claim 67, wherein said noise comprises a homogeneous function in frequency space.
69. The apparatus of claim 66, wherein said analyte filter comprises:
a multi-stage filter.
70. The apparatus of claim 69, wherein said multi-stage filter comprises:
a two-stage filter.
71. The apparatus of claim 66, wherein said analyte filter is generated theoretically.
72. The apparatus of claim 66, wherein said filter comprises:
average attenuation of less than 0.05 magnitude above 0.25 frequency units.
73. The apparatus of claim 72, wherein said filter comprises:
a maximum gain of less than 0.1 magnitude above 0.25 normalized frequency units.
74. The apparatus of claim 73, wherein said average attenuation comprises a value less than 0.025 magnitude and said maximum gain comprises a value less than 0.05 magnitude.
75. The apparatus of claim 66, wherein said analyzer comprises:
a sample module in a first housing; and
a base module in a second housing, wherein said sample module communicates with said base module.
76. The apparatus of claim 66, wherein said analyzer comprises:
a photo-diode array.
77. The apparatus of claim 66, wherein said analyzer further comprises:
a coupling fluid; and
a guide to acquire, wherein said coupling fluid and said guide couple said sample module to a tissue sample during use.
78. The apparatus of claim 66, wherein said analyte filter is generated with a set of spectrometers, wherein said set of spectrometers does not comprise said analyzer.

* * * * *